(12) United States Patent
Santini et al.

(10) Patent No.: US 8,695,891 B2
(45) Date of Patent: Apr. 15, 2014

(54) DUAL FUNCTIONING FRAGRANCE DELIVERY DEVICE

(75) Inventors: Thomas Santini, Rockleigh, NJ (US);
Anthony Budraitis, Rockleigh, NJ (US);
Charles Steward, Rockleigh, NJ (US);
John Gick, Rockleigh, NJ (US)

(73) Assignee: Takasago International Corporation, Tokyo (JP)

( * ) Notice: Subject to any disclaimer, the term of this patent is extended or adjusted under 35 U.S.C. 154(b) by 598 days.

(21) Appl. No.: 12/897,316

(22) Filed: Oct. 4, 2010

(65) Prior Publication Data

US 2011/0079658 A1 Apr. 7, 2011

Related U.S. Application Data

(60) Provisional application No. 61/248,231, filed on Oct. 2, 2009, provisional application No. 61/295,429, filed on Jan. 15, 2010.

(51) Int. Cl.
*A24F 25/00* (2006.01)
*A61L 9/04* (2006.01)

(52) U.S. Cl.
USPC .............. 239/44; 239/34; 239/53; 239/54; 239/57; 239/60

(58) Field of Classification Search
USPC ........... 239/34, 44, 45, 46, 47, 51, 53, 54, 55, 239/57, 60, 289
See application file for complete search history.

(56) References Cited

U.S. PATENT DOCUMENTS

| | | | |
|---|---|---|---|
| 4,323,193 A * | 4/1982 | Compton et al. ............ 239/44 |
| 4,529,376 A | 7/1985 | Cafolla | |
| D331,727 S | 12/1992 | Grosfillex | |
| 5,840,257 A * | 11/1998 | Bureau et al. .............. 422/125 |
| 6,152,728 A | 11/2000 | Griffel | |
| 6,555,069 B1 * | 4/2003 | Ferguson .................. 422/126 |
| 6,569,387 B1 | 5/2003 | Furner et al. | |
| D489,501 S | 5/2004 | Dretzka | |
| 7,467,945 B2 | 12/2008 | Kubicek et al. | |
| 2002/0114904 A1 * | 8/2002 | Chang ..................... 428/34.1 |
| 2005/0271994 A1 | 12/2005 | Furner | |
| 2006/0024629 A1 | 2/2006 | Rivard | |
| 2006/0078477 A1 | 4/2006 | Althouse et al. | |
| 2006/0231641 A1 | 10/2006 | Uchiyama et al. | |
| 2007/0290065 A1 * | 12/2007 | Brown et al. ................ 239/44 |
| 2011/0280009 A1 | 11/2011 | Krause | |

FOREIGN PATENT DOCUMENTS

| | | |
|---|---|---|
| GB | 2395126 | 5/2004 |
| WO | WO84/04459 | 11/1984 |
| WO | WO2008/042237 | 4/2008 |
| WO | WO2009/073813 | 6/2009 |
| WO | WO2009/152502 | 12/2009 |

OTHER PUBLICATIONS

U.S. Appl. No. 13/495,933, filed Jun. 13, 2012.
U.S. Appl. No. 29/376,230, Aug. 7, 2012 Issue Fee payment.
U.S. Appl. No. 29/376,230, May 9, 2012 Notice of Allowance.
U.S. Appl. No. 29/376,230, filed Oct. 4, 2010.
European Search Report for EP 10251731, dated Jul. 27, 2011.

* cited by examiner

*Primary Examiner* — Ryan Ries
(74) *Attorney, Agent, or Firm* — Baker Botts L.L.P.

(57) ABSTRACT

A fragrance delivery device that includes a hollow vessel containing a first fragrance medium and further comprising a porous exterior surface with a porous wicking extension extending therefrom; and a reservoir containing a second fragrance medium, the second fragrance medium in fluid communication with the wicking extension.

22 Claims, 21 Drawing Sheets

DUAL FUNCTIONING FRAGRANCE DELIVERY DEVICE

The present application claims the benefit of U.S. Application No. 61/248,231, filed Oct. 2, 2009 and U.S. Application No. 61/295,429, filed Jan. 15, 2010, each of which are hereby incorporated by reference in their entirety.

FIELD

The present application provides a dual functioning fragrance delivery system.

BACKGROUND

A number of methods exist for dispensing a volatile fragrance material into the air in order to create a pleasant indoor fragrance experience and/or for the purpose of counteracting or neutralizing offensive odors. Previous methods utilizing vessels made from porous materials such as ceramic, have been used as a means to provide fragrance dispersion. Typically, these products are offered with a pre-measured amount of fragrance which is simply poured into the vessel in order to initiate activation. Migration of the fluid fragrance into the absorbent vessel completes the process. A glazing on the outside of the vessel protects surfaces from unwanted exposure to the fragrance.

Previously, there have been devices created to combine various technologies with candles. Some of such devices have been created for distributing fragrance. Most commonly the candle has been used as a heat source to evaporate the volatiles from gels, liquids, waxes on absorbent substrates that are positioned above the flame or in close proximity to it. Although being effective to an extent, these devices also suffer from being fully functional only while the candle is lit.

Gels, although continuous in their odor producing capabilities, have frequently lacked a sustainable fragrance intensity that is consistent throughout their functional lives. The performance profile for gels typically generates good fragrance awareness early; however, this odor awareness dissipates quickly to imperceptible levels shortly after activation. This inconsistent performance by gels has been a significant drawback to their success in the marketplace.

Both candles and gels offer economic methodologies for use as fragrance dispersion mediums and if their performances could be improved, a much wider acceptance of the forms of air freshening would be achieved.

Candles, while offering a relatively inexpensive means to achieve fragrance dispersion, exhibit limitations preventing them from effectively operating in a continuous manner. The volatilization of fugitive fragrance materials occurs primarily when the candle is lit and the candle composition is melted to create a molten pool. The elevated temperature that occurs in this pool hastens the diffusion of the volatiles into the surrounding environment. Very little fragrance is emitted from the candle when it is not lit, only that which is available from any of the candle's exposed surfaces.

Candles are generally not continuously operational throughout their lifetimes. This is largely because of the safety concern created by having an unsupervised open flame. In addition, the continuous operation would greatly reduce the functional life of the candle. In the case of creating a continuous indoor fragrance experience, the intermittent operation of the candle does not allow for the sufficient release of volatiles to create a seamless fragrance impression.

Accordingly, there is a need and desire for a dual functioning fragrance delivery system capable of emitting volatile liquid mixtures, for example a fragrance, from two independently sourced fragrance mediums.

SUMMARY

It is the object of the present disclosure to demonstrate an improved method for dispensing fragrance that utilizes two independent fragrance mediums, and devices for the same. For example, it is an object to utilize the vessel not only as the housing for containing one fragrance medium (e.g., a candle), but also to have the same vessel act as its own source of a second fragrance medium (e.g., a gel or liquid fragrance composition). Optionally, the vessel can also hold a self-contained air freshening form such as polymer beads that can be inserted into the hollow void of the vessel while remaining encased in their own container.

One embodiment of the present application provides a fragrance delivery device that includes a hollow vessel containing a first fragrance medium and further comprising a porous exterior surface with a porous wicking extension extending therefrom; and a reservoir containing a second fragrance medium, the second fragrance medium in fluid communication with the wicking extension. In various embodiments, the first fragrance medium (e.g. candle) is generally disposed, in a physical sense, over the second fragrance medium. The first fragrance medium and the second fragrance medium can be concentric.

Another embodiment of the present application provides a fragrance delivery device that includes a hollow vessel containing a first fragrance medium and further comprising a porous exterior surface; a member comprising a porous wicking extension, the member adapted to engage with the hollow vessel; and a reservoir containing a second fragrance medium and adapted to engage with the member comprising a porous wicking extension, the second fragrance medium in fluid communication with the wicking extension.

Embodiments of the present application also provide a method of dispensing a fragrance that includes employing any one of the fragrance delivery devices of the present application.

DETAILED DESCRIPTION

Figure 1:
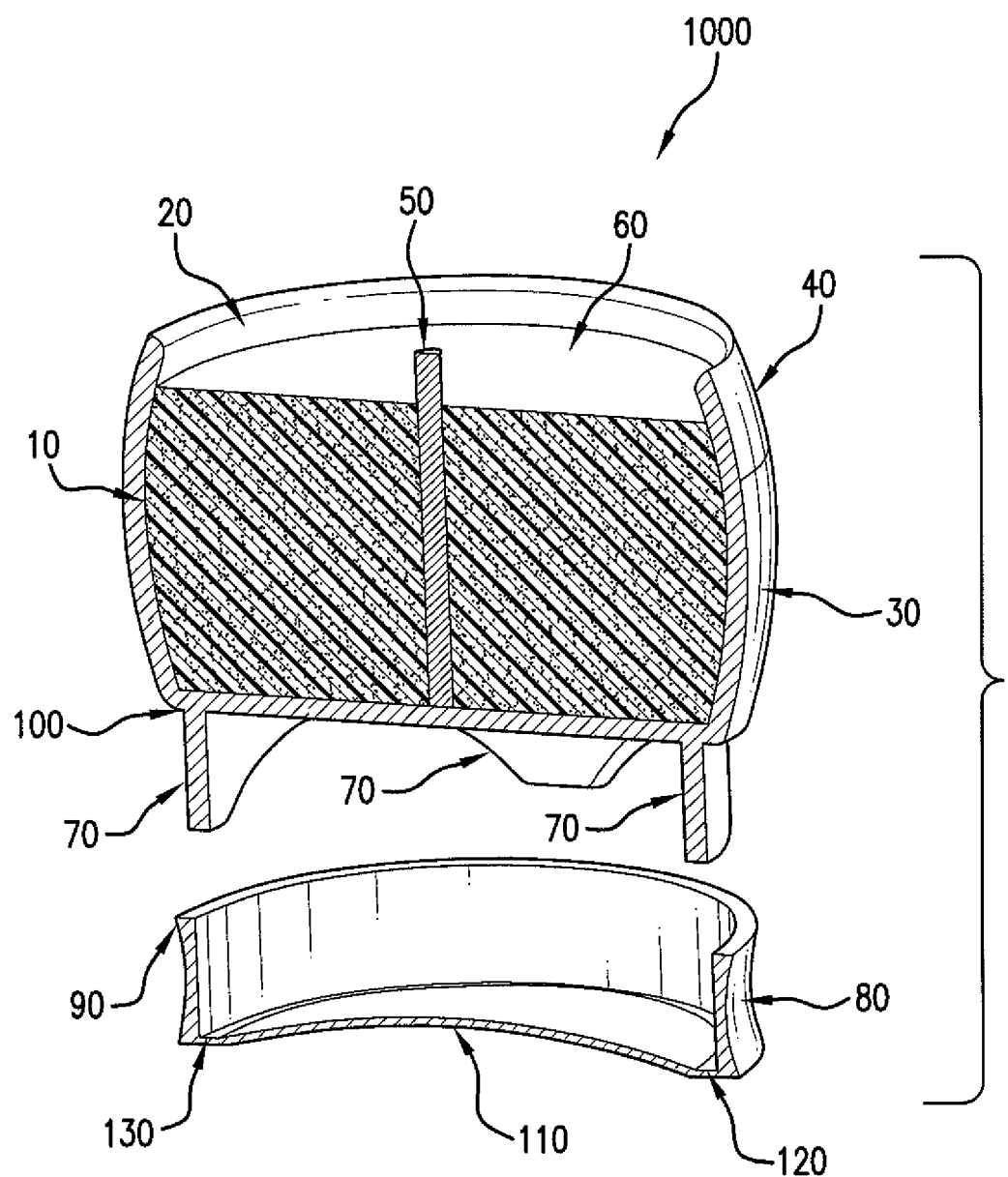
FIG. 1 depicts a fragrance delivery device according to one embodiment of the present application in which a candle is provided as the first fragrance medium, and a liquid fragrance composition housed in a reservoir base is provided as the second fragrance medium.

One or more objects of the present application are accomplished by the provision of a dual functioning fragrance delivery system that includes:

(a) a vessel either wholly or partially fabricated from a porous composition and having a porous surface;

(b) a first fragrance medium, such as a candle, capable of being housed in the fragrance delivery system and;

(c) a second fragrance medium, such as a gel or liquid fragrance composition, that is capable of being loaded within in a reservoir of the fragrance delivery system;

(d) at least one wicking extension from the porous surface of the vessel located at or near its base that extends downward for eventual engagement with the reservoir and capable of wicking the contents of the reservoir.

In various embodiments, the reservoir can be a detachable reservoir base sized such that it can accept the full contents of the fluid reservoir composition as well as the extensions of the vessel. Preferably the extension that will rest within the confines of the base and have intimate and complete contact with the contents of the reservoir. The vessel can be a hollow vessel, and the hollow vessel can be optionally be further loaded with a third fragrance medium, such as polymeric beads.

In one embodiment, a liquid or gel fragrance composition is charged into the reservoir base and the hollow vessel is oriented directly over, or substantially directly over, said base with the porous extensions at least partially disposed in the liquid or gel fragrance composition. Preferably, the vessel is lowered onto the loaded reservoir base until it comes to engage the base with the wicking extensions resting on the bottom of the reservoir base. In various embodiments, the vessel is additionally supported by the engagement of the elevated sidewalls of the reservoir base with an accepting recess formed into the side of the vessel. The fluid reservoir composition first enters the porous extensions of the vessel for evaporation into the atmosphere from the porous surface of the vessel. Fragrance is also dispersed from the first fragrance medium (e.g., a gel or candle contained within the void of the vessel interior), creating a dually sourced fragrance dispenser.

Thus, in various embodiments, the dual functioning fragrance delivery system of the present application offers the advantage of being able to serve as the container for a first fragrance medium such as a gel composition or candle, while at the same time providing a source for a second, independent fragrance medium, such as a liquid composition (e.g., essential oils) or, in alternative embodiments, a solid fragrance composition (e.g., potpourri). In some embodiments, the fragrance emitted from the first fragrance medium, and the fragrance emitted from the second fragrance medium, while pleasing alone, are, as combined, designed to provide a synergistically pleasing fragrance to a consumer.

In embodiments in which the second fragrance medium includes a liquid or otherwise diffusible fragrance composition, the partial immersion of the vessel into the detachable reservoir base that contains the second fragrance composition (e.g., a fluid reservoir fragrance composition) results in the transfer of the second fragrance composition into the absorbent porous surfaces of the vessel which holds the first fragrance composition. In various embodiments, evaporation of the fugitive fragrance materials (i.e., the second fragrance composition) from the porous surface of the vessel results in a very effective fragrance dispersion method.

The combination of fragrance diffusion from the surface of the vessel as well as that emanating from first fragrance composition contained within the vessel offers significant advantages as compared to those fragrance dispersion methods that rely on a single source.

The application will now be described in reference to the drawings. FIG. 1 depicts an embodiment of the present application (1000). The exploded crosscut view of the unit depicted in FIG. 1 provides a candle (60) as the first fragrance medium which is supported on a reservoir that forms the base (80) of the device.

The unit includes a hollow vessel (10) made from a porous material such as ceramic. Other non-limiting examples of the hollow vessel material, besides a ceramic, include, but are not limited to terracotta, clay earthenware, concrete and porcelain. A glazed coating can be applied to the surface of vessel, including a glazed interior coating (20) and a glazed exterior coating (40) that can be positioned so as to allow a consumer to handle the vessel without coming into contact with the contents of the reservoir that will diffuse into the porous sidewalls of the vessel (30).

A candle wick (50) is centrally positioned in the vessel prior to the loading of the molten candle composition which forms a candle (60) upon cooling (e.g., a solid or semi-solid candle upon cooling). Wicking extensions (70) protrude downward from the base of the vessel and are generally along the same plane as the vessel's sidewalls (30).

A detachable reservoir base (80), upon which the vessel rests, is composed of a material such that when the liquid reservoir composition is loaded into it, and there is no permeation through the reservoir base. Suitable compositions for said base would include, but are not limited to, any porous materials with a glaze applied thereto, such as a glazed ceramic, terracotta, clay earthenware, concrete or porcelain substrate. Thermoplastic or thermoformed compositions such as, but not limited to, polypropylene, polyethylene, polyethylene terephthalate and the like, would also prove a suitable material for the reservoir base.

The reservoir base (80) is sized proportionately to receive the full amount of the fluid reservoir composition, as well as be sufficiently sized to accept the wicking extensions (70)

protruding from the base of the vessel. The upper lip of the reservoir base (90) can engaged into a recess (100) formed in the body of the vessel to accept it.

The reservoir base (80) can be optionally provided with an elevated interior center so as to yield a domed convex surface (110). This elevated center gradually tapers down to the channel edge (120) of the recessed channel (130).

Figure 2:
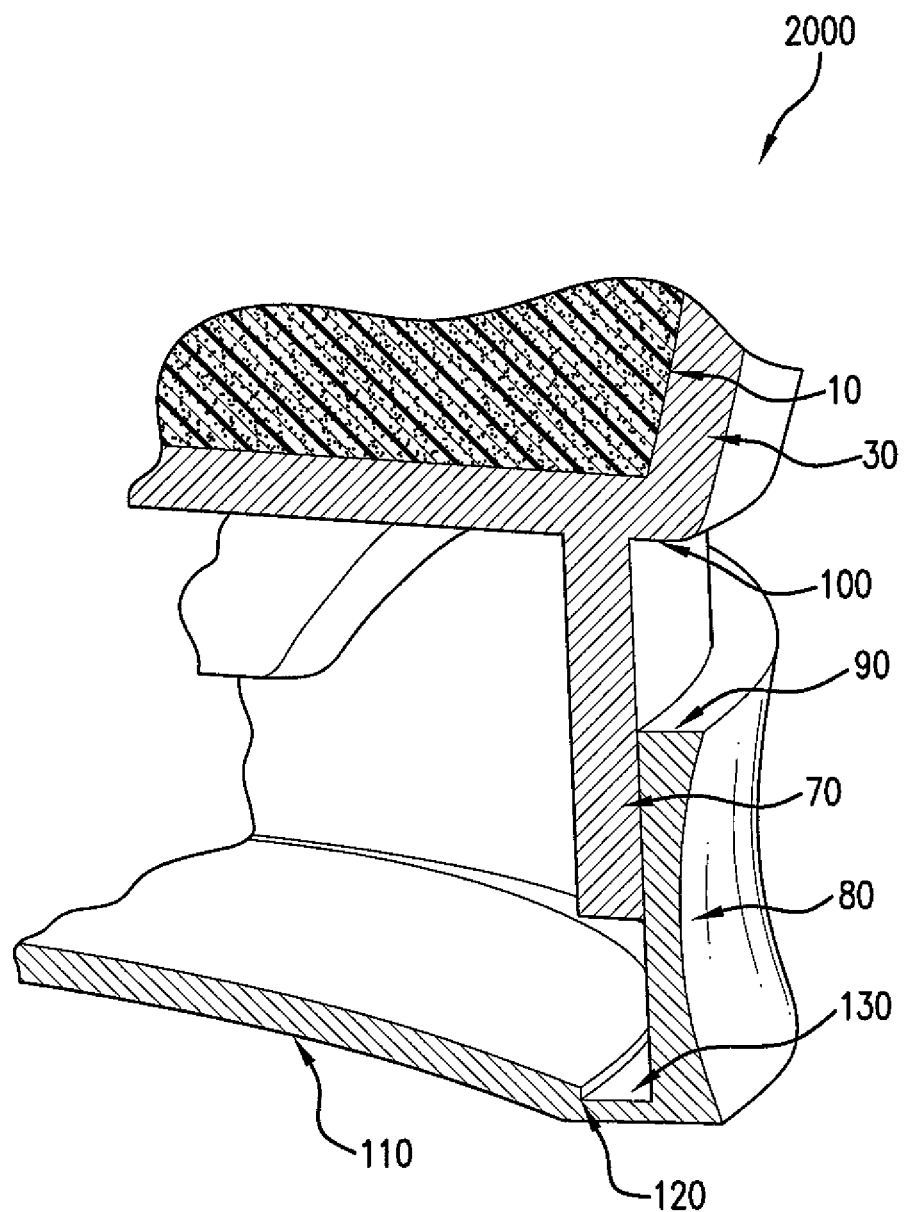
FIG. 2 depicts a close-up view of the engagement of the hollow vessel with the reservoir base according to one embodiment of the presently disclosed subject matter.

FIG. 2 is an enlarged crosscut view (2000) of the base of the device of FIG. 1, which includes a recessed channel (130) that fully circumscribes the outermost circumference of the reservoir base (80) and is of sufficient width to have the wicking extensions (70) reside in the recess formed by the recessed channel (130) and to rest in flush contact with the bottom reservoir base. Alternatively, the wicking extensions can be sized so as to, when fully engaged, rest short of the bottom of the reservoir base, although it is preferred that the wicking extensions rest on the recessed channel itself when fully engaged.

The convexed surface (110) of the reservoir base center will direct the fluid reservoir composition (not shown) toward the wicking extensions (70) and maximize the contact between the wicking extensions and the reservoir fluid. A channel edge (120) is also provided, and preferably spaced at such a distance to engage the wicking extension.

FIG. 2 also shows a detailed view of the hollow vessel (10) containing porous vessel sidewalls (30). A recess (100) is provided along the bottom of the hollow vessel for engagement with the reservoir base upper lip (90).

Figure 3:
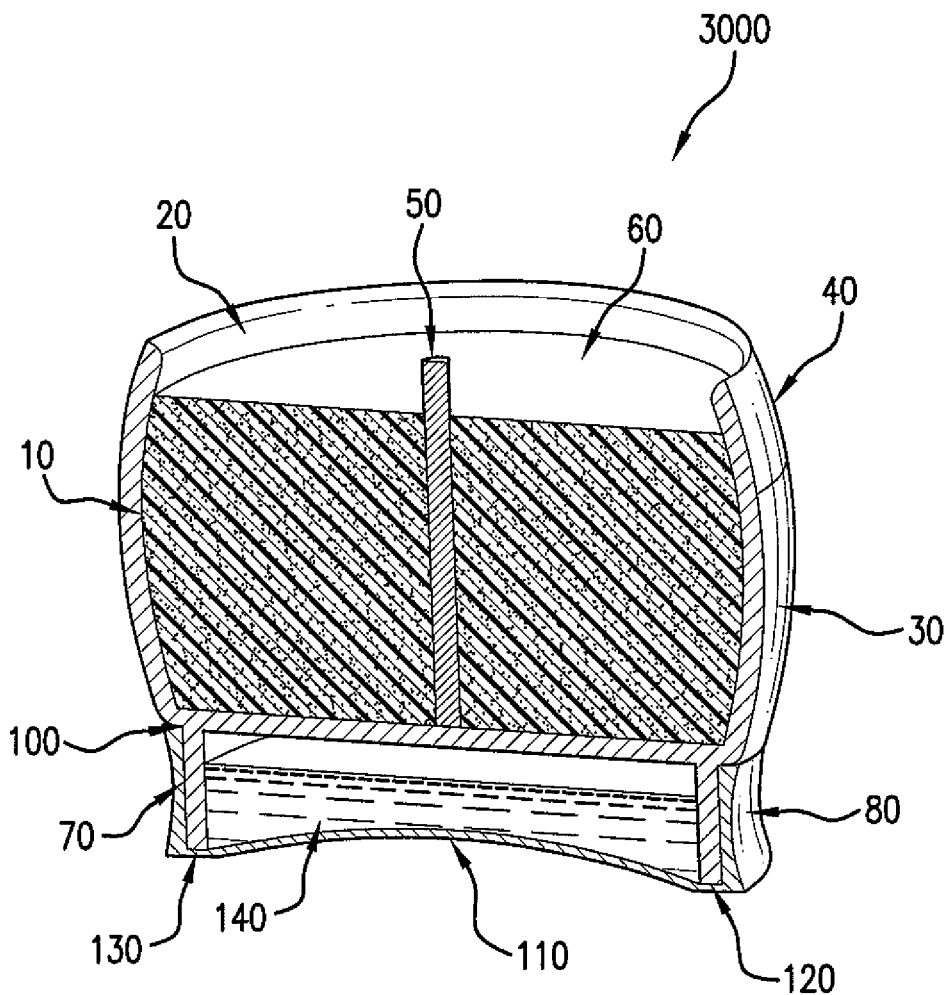
FIG. 3 depicts a view of a fragrance delivery device of one embodiment of the present application, in which the reservoir is shown loaded with a liquid fragrance composition.

FIG. 3 is a crosscut view (3000) depicting the engagement of the hollow vessel (10) with the reservoir base (80) after the liquid reservoir composition (140) has been loaded into the reservoir base in a separate process (not shown). The engaging of the vessel (10) with the reservoir base (80) will cause the wicking extensions (70) to rest in the recessed channel (130) formed to accept them and to come into intimate contact with the reservoir liquid composition (140). Migration of the fragrance composition out of the reservoir base (80) and into the vessel's porous absorbent sidewalls (30) will continue until the reservoir fluid in the reservoir base is depleted or until the vessel's sidewalls (30) are fully saturated.

The diffusion of the volatile components of the reservoir composition (140), the result of their exposure to the expanded surface offered by the vessel's porous sidewalls (30), results in a highly effective emanating process for the creation of a fragranced indoor environment.

FIG. 3 also depicts a recess (100) which serves to position the wicking extension (70) inside the sidewall of the reservoir base (80) and within the recessed channel edge (120). The reservoir base is provided with a convex surface (110) along the bottom of the reservoir in order to direct the reservoir liquid composition (140) to the wicking extensions (70). The hollow vessel, which is porous, is coated with a glazed coating exterior (40) and a glazed coating interior (20) for purposes of aesthetics and to facilitate handling of the device. Although this device is shown with a candle (60) and candle wick (50), the hollow vessel (10) can alternatively hold, for example, a gel composition as an independent fragrance medium in addition to the reservoir liquid composition (140).

Correspondingly, the ability to create an intense fragrance environment is additionally supported by the use of the candle contained within the vessel as an additional means to achieve fragrance diffusion. The dual benefit derived by having two independent sources of fragrance in a single unit results in performance characteristics that are superior to those generated from either one of these methodologies being used exclusive of the other.

Figure 4:
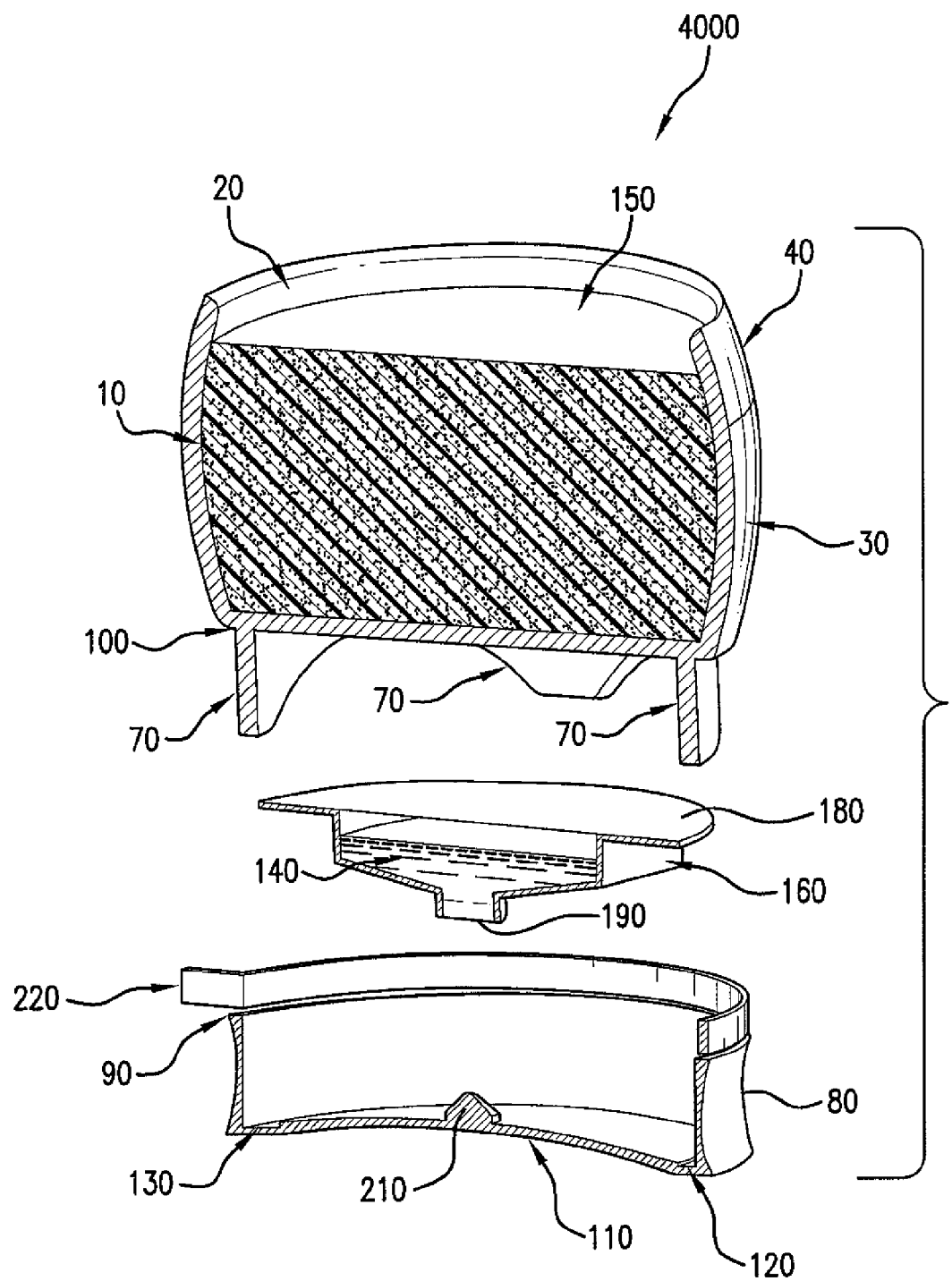
FIG. 4 depicts an alternative embodiment of the presently disclosed subject matter, in which a fragrance cartridge is provided for ultimate engagement with a piercing lance.
Figure 5A:
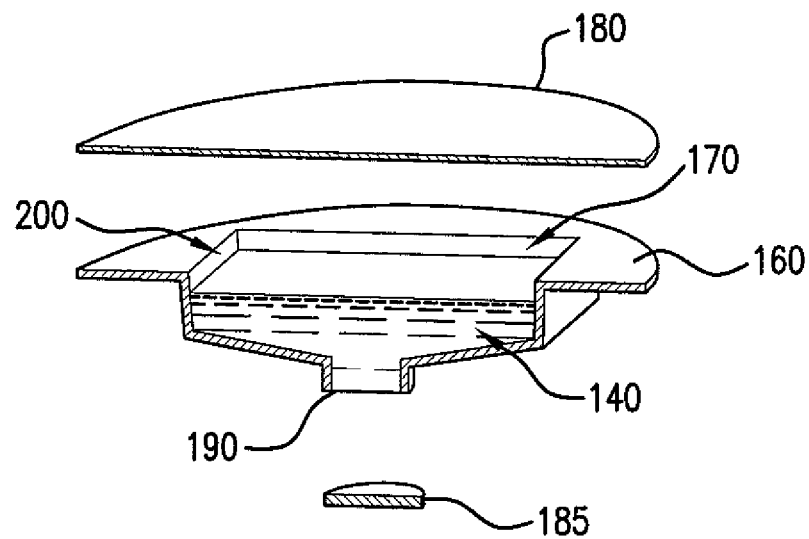
FIG. 5 depicts close-up views of the fragrance cartridge, provided with top and bottom rupturable foil seals.
Figure 5B:
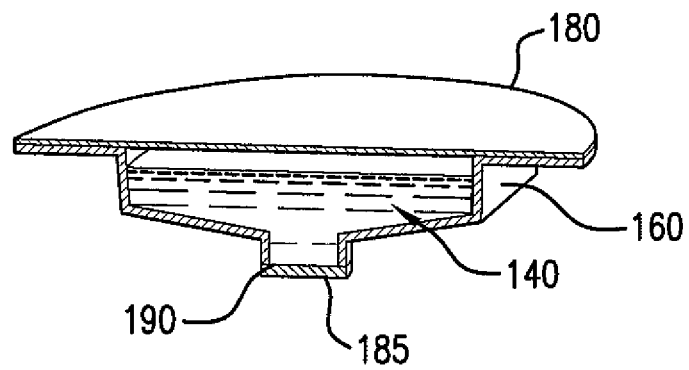

The exploded crosscut view of the unit (4000) depicted in FIG. 4 shows a hollow vessel (10) made from a porous material such as ceramic. The wicking extensions (70) are again shown at the base of the vessel (10) and are continuous with the porous vessel's sidewalls (30), but oriented inside the sidewalls due the recess (100).

The hollow vessel (10) in this embodiment can be used as a container for a fragranced gel composition (150). Fragranced air freshening gels can be formed by the use of either naturally derived hydrocolloids such as carrageenan or gellan gums for use in aqueous based compositions, metallic salts such as sodium stearate for water, glycol compositions, or through the use of synthetic polymers such as thermoplastic elastomers, polyurethane and polyamides, for anhydrous or substantially anhydrous fragrance solvent systems. Alternatively, another fragrance medium could be housed in the hollow vessel, such as, but not limited to, potpourri, fragranced soaps, and fragranced polymer beads.

The gels can be poured into the hollow vessel either as heated liquefied fluids such that upon cooling they set into a final solid or semi-solid form or they can be poured at ambient temperature and through a cross-linking process develop into their final gel-like consistency over a period of time.

The vessel (10) is glazed with an impervious glazed surface coating (20) covering the interior of the vessel to provide an aesthetically appealing appearance. A portion of the glazing (40) is also used on the outer surface of the vessel to facilitate handling. The gel composition (150) is loaded into the hollow vessel (10) and allowed to set until such time as the gel achieves its final, desired consistency.

FIG. 5 depicts a close-up view of the reservoir insert (160) also shown in FIG. 4, which is provided with a rupturable top foil seal (180) and a rupturable bottom foil seal (185). Reservoir insert (160) can be made of, for example a thermoplastic, which can be prepared, for example, by injection molding or thermoforming processes known to those of ordinary skill in the art. The cavity (170) formed in the reservoir insert (160) is sized such that it is capable of containing the full measure of the liquid reservoir composition (140). The reservoir is formed with two openings. A heat sealable material (185) that is capable of being ruptured is sealed over the narrower of the two openings (190). The liquid fragrance reservoir composition (140) is then loaded into the cavity (170) via filling through the larger opening (200).

Figure 8:
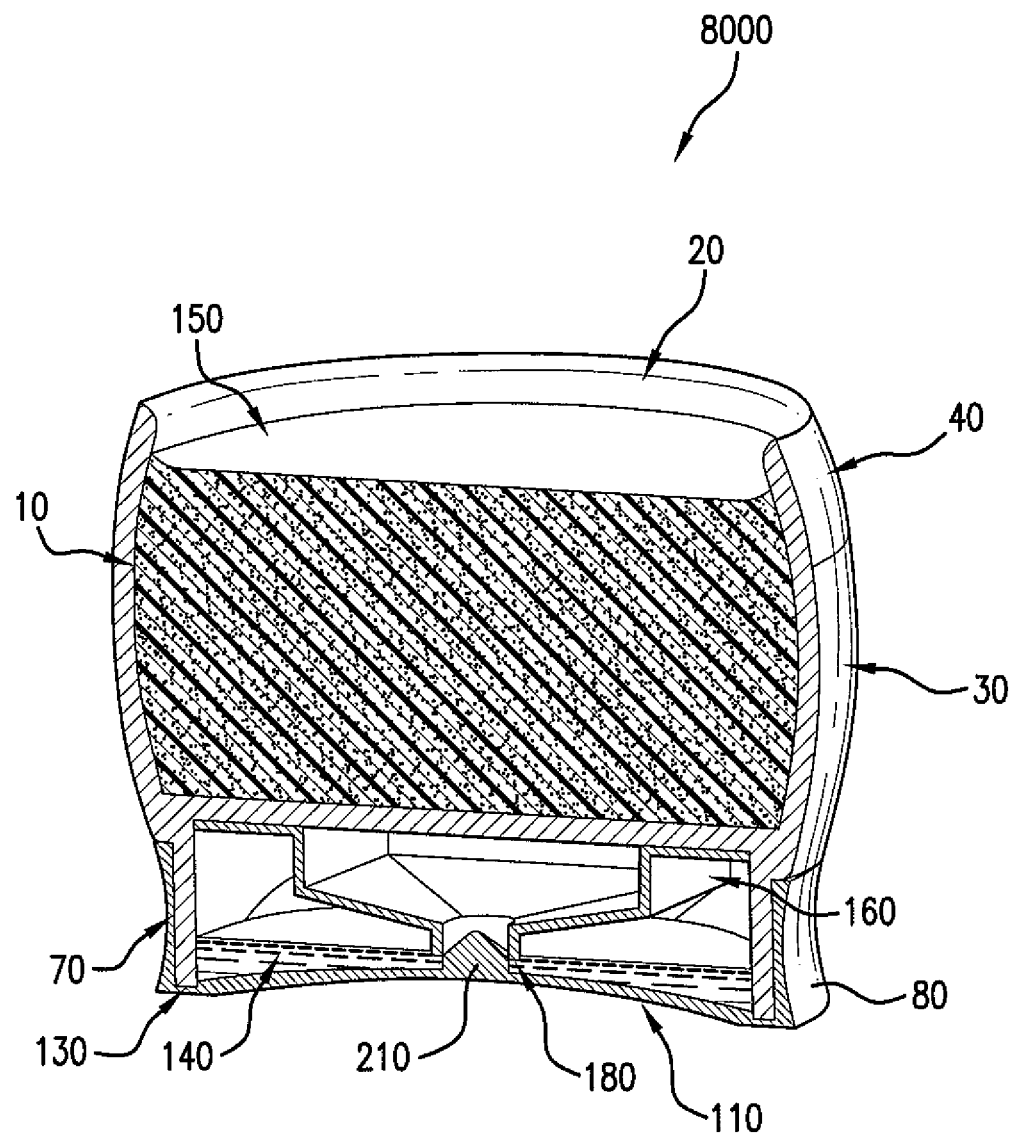

Once the reservoir container is loaded, a heat sealable material (180) is affixed over the larger opening (20), sealing the fragrance composition (140) within the cavity (170). The reservoir container can then be adhesively or mechanically inserted into the space formed in the vessel (10) to accept it as depicted in FIG. 8.

Referring back to FIG. 4, the reservoir insert (160) is oriented such that the narrow opening (190) is directed towards the reservoir base (80). The reservoir base (80) provides a domed convex center (110) on top of which is a piercing lance (210). This piercing lance (210) is ideally formed as part of the injection molding process used to manufacture the reservoir base (80). The reservoir base (80) also exhibits in this embodiment a tear-away band (220) that runs continuously around the top of the reservoir base (80) and is formed as part of the same injection molding process in which the reservoir base (80) is formed. The tear-away band (220) serves the function of keeping the piercing lance (210) from contacting the reservoir insert (160) positioned above it and causing unwanted activation of the unit. Removal of the tear-away band (220) allows the reservoir base (80) to travel upward such the recess (100) will rest on the reservoir upper lip (90)

and so that the piercing lance (210) can now engage the foil seal (not shown in FIG. 4) covering the narrow opening (190) of the reservoir insert (160).

Activation of the unit is effected when the hollow vessel (10) is forcibly engaged with the reservoir base (80) and in the process causing the piercing lance (210) to rupture the foil seal (180) oriented above it and thereby allowing the fluid contents (140) of the reservoir insert (160) to drain into the reservoir base (80). The fluid fragrance composition will then come in intimate contact with the wicking extensions (70). Positioning of the wicking extension within the base is added by a recessed channel in the base (130) which is provided with a recessed channel edge (120).

The reservoir liquid composition will absorb upwards into the absorbent porous surfaces of the hollow vessel (10). Fragrance is then dispersed into the surrounding environment by the evaporation of the volatile components from the surfaces of the vessel. Fragrance diffusion is augmented by the contribution of the fragranced gel contained within the hollow vessel.

Figure 7:
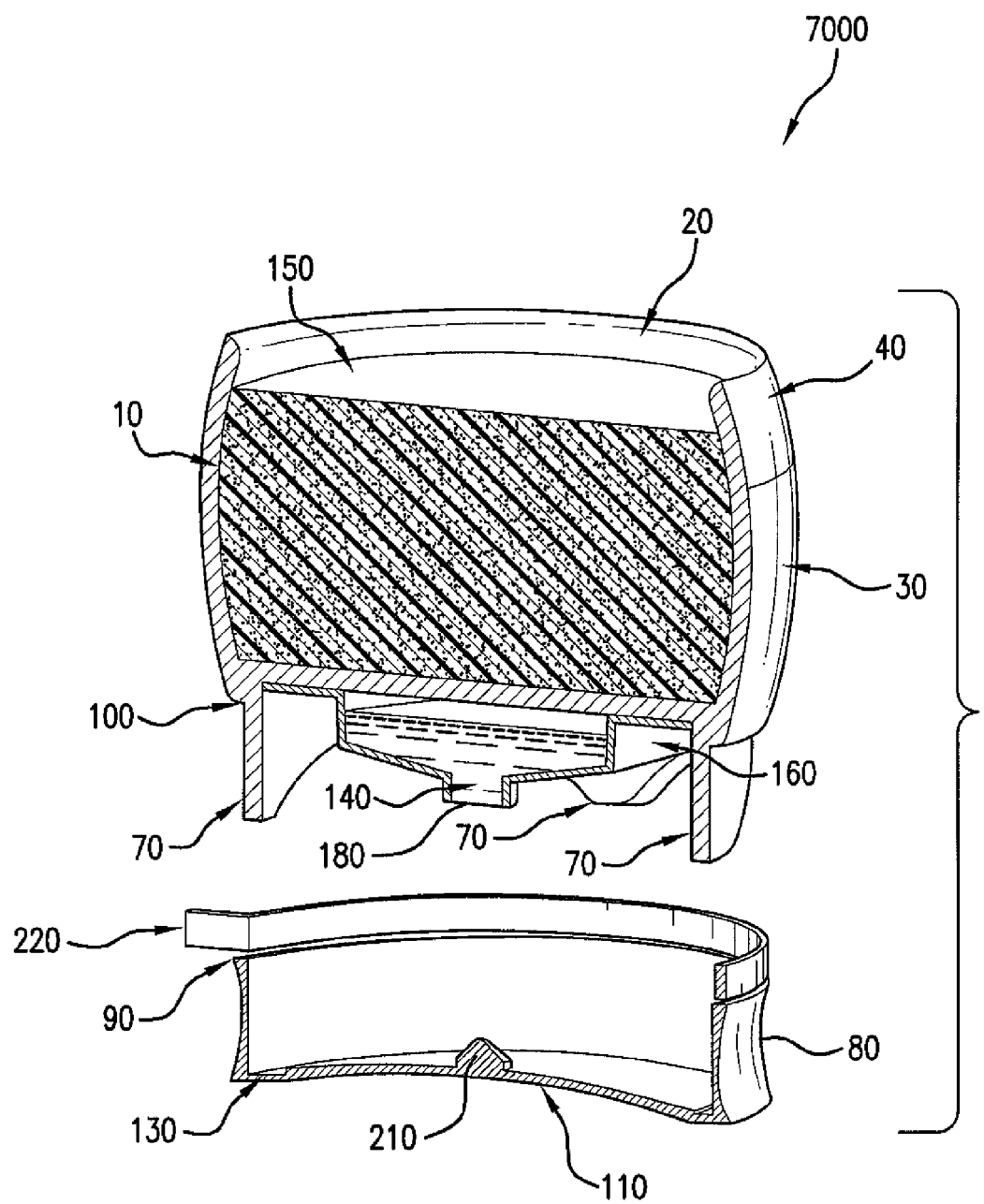
FIGS. 7 and 8 depict exploded and as-combined views of a fragrance delivery device of the present application in which a gel composition is provided as the first fragrance medium.

FIG. 7 depicts another device (7000) that is provided with a reservoir insert (160) secured to the bottom of the hollow vessel (10) and positioned for ultimate engagement with a piercing lance (210). The reservoir insert can be secured to the bottom of the vessel by any appropriate means known to those of ordinary skill in the art. Due to the recess (100), the wicking extensions (70) fit just inside the sidewalls of the reservoir base. Upon removing the tear away band (220), the recess (100) will rest on the reservoir base upper lip (90), and the wicking extensions will be disposed in the recessed channel (130) which is provided along the periphery of the bottom of the reservoir base. Prior to removing the tear away band, the sealed bottom of the reservoir insert (180) does not engage with the piercing lance, and the contents of the reservoir insert remain inside. The bottom of the reservoir base is provided with a convex surface (110) so that, once deployed, the reservoir liquid composition will be directed towards the recessed channel and wicking extensions.

Although the device of FIG. 7 is shown with a gel composition (150), other fragrance mediums can be housed in the hollow vessel. In some embodiments the reservoir liquid composition (140), which will diffuse out of the porous vessel sidewall (30), is designed to synergistically interact with the gel composition (150) to provide a pleasing, long-lasting fragrance to the ambient space around the device. As discussed above, the device is provided with a glazed coating interior (20) and exterior (40).

FIG. 8 provides another view of a device (8000) that is provided with a reservoir insert (160). As shown, the reservoir liquid composition (140) has been deployed, as the piercing lance (210) has ruptured the foil seal (180). The device is also provided with a hollow vessel (10), having a porous sidewall (30) and loaded with a gel composition (150), glazed coating along portions of the interior (20) and exterior (40), wicking extensions (70), a reservoir base (80) with a convex bottom surface (110), and a recessed channel (130).

Figure 9:
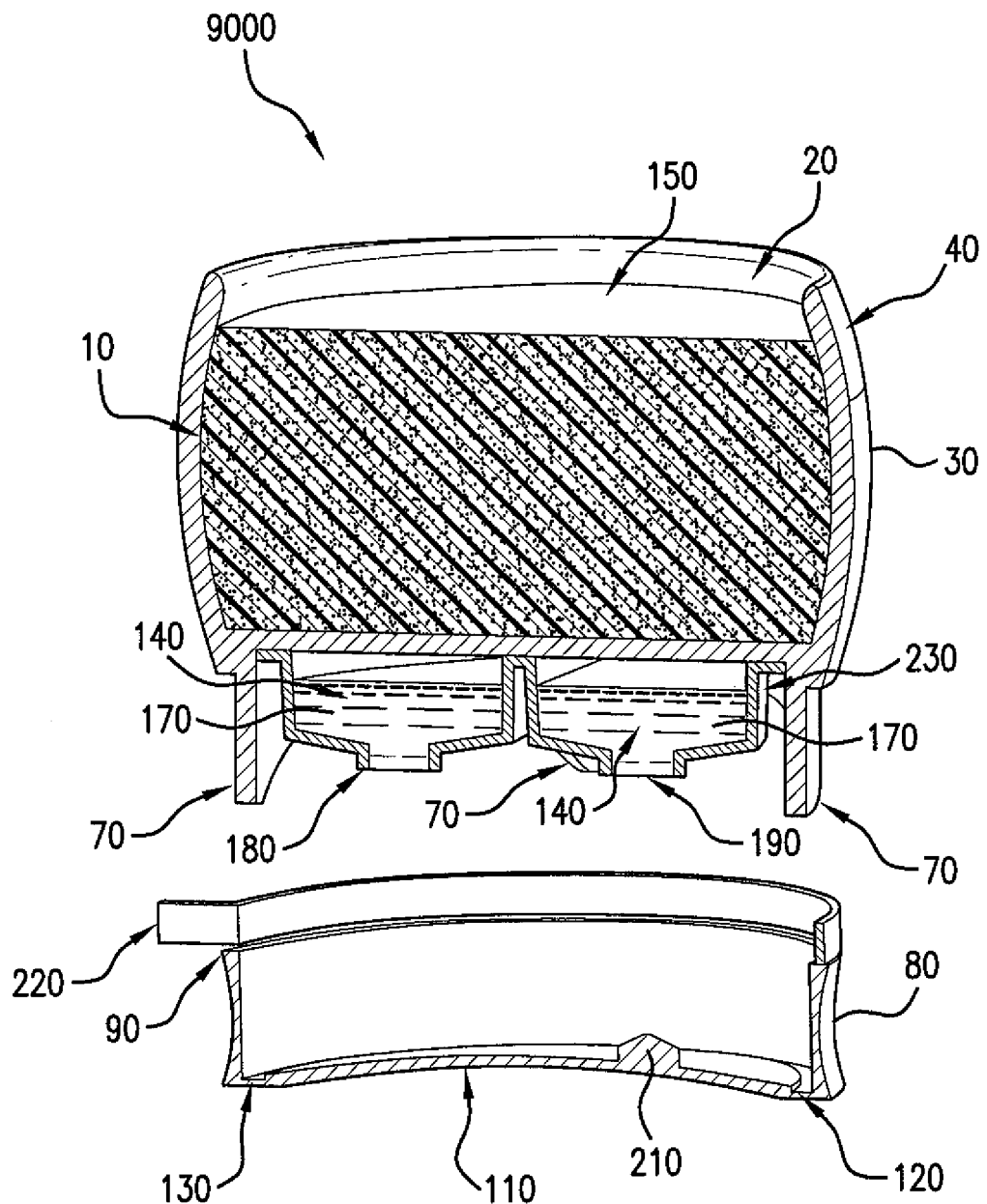

An additional embodiment of a fragrance delivery device (9000) according to the present application is depicted in FIG. 9. This embodiment provides a dual cavity reservoir insert (230) capable of containing the reservoir composition (140) of a single fragrance or that of two different fragrances in the cavities (170) of the dual cavity reservoir insert (230). One benefit of having a reservoir insert capable of containing two fragrance compositions is that, as the fragrance emanation generated by the fragrance composition contained in the first reservoir dissipates over time, the contents of the second cavity can be released to renew the scent producing characteristics of the unit. The option of using two different fragrances in the dual cavity reservoir insert (230), in addition to the independent fragrance medium contained in the hollow vessel (10) (here a gel composition (150)), affords the user a more varied fragrance experience.

The device of FIG. 9 also contains a glazed coating along portions of the exterior (40), and interior (20) of the porous vessel sidewall (30). Also provided is a narrow opening (190), capped with a foil seal (180). Wicking extensions (70), sized to engage with a recessed channel (130), formed with a recessed channel edge (120) is also provided. The reservoir base (80) is provided with a reservoir base upper lip (90) and a convex surface (110) along the bottom to direct the reservoir liquid composition, once employed, to the recessed channel.

Figure 6A:
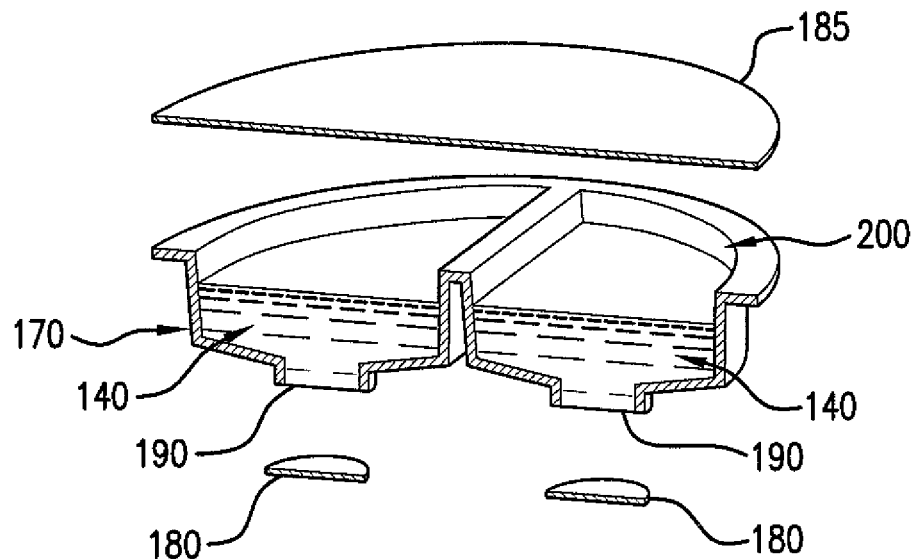
FIGS. 6 and 9 depict a still further alternative embodiment, in which dual fragrance cartridges are provided.
Figure 6B:
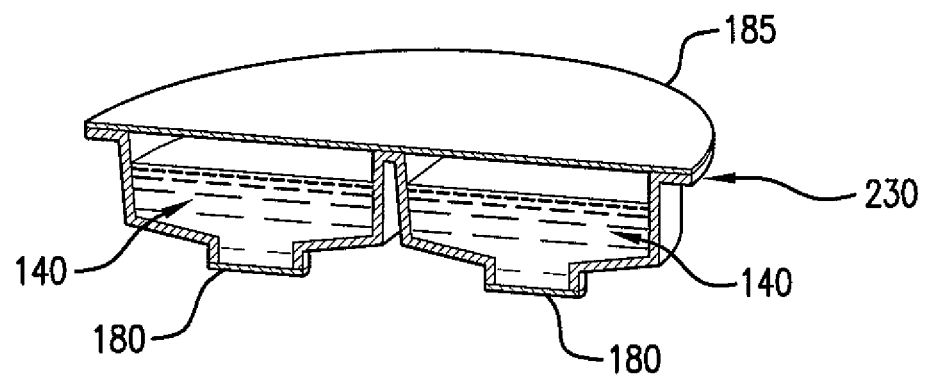

Referring now to FIG. 6, a dual cavity reservoir insert (230) according to one embodiment of the present application is formed from a thermoplastic material. The thermoplastic material can be manufactured, for example, by an injection molding or thermoforming process. The dual cavity reservoir insert (230) is formed with four openings defining the formation of two cavities (170). The narrower openings (190) are closed with a heat sealable, rupturable foil seal material (180). The reservoir liquid composition (140) is loaded into the cavities (170) and a heat sealable top foil seal covering (185) is used to close the larger openings (200). The dual cavity reservoir insert (230) is then affixed to the base of the vessel and oriented with the narrow openings (190) directed towards the reservoir base.

Referring now to FIG. 9, once the tear-away band (220) is removed, the engagement of the hollow vessel (10) with the reservoir base (80) results in the rupturing of the foil closure (180) by the piercing lance (210).

In this embodiment, since the narrow cavity openings (190) are off center, the piercing lance (210) is also positioned off center to engage the openings. The option of rotating the reservoir base (80) to have the piercing lance (210) positioned properly to rupture the seal of the second cavity would require that only one piercing lance (210) be molded into the reservoir base (80).

Figure 10:
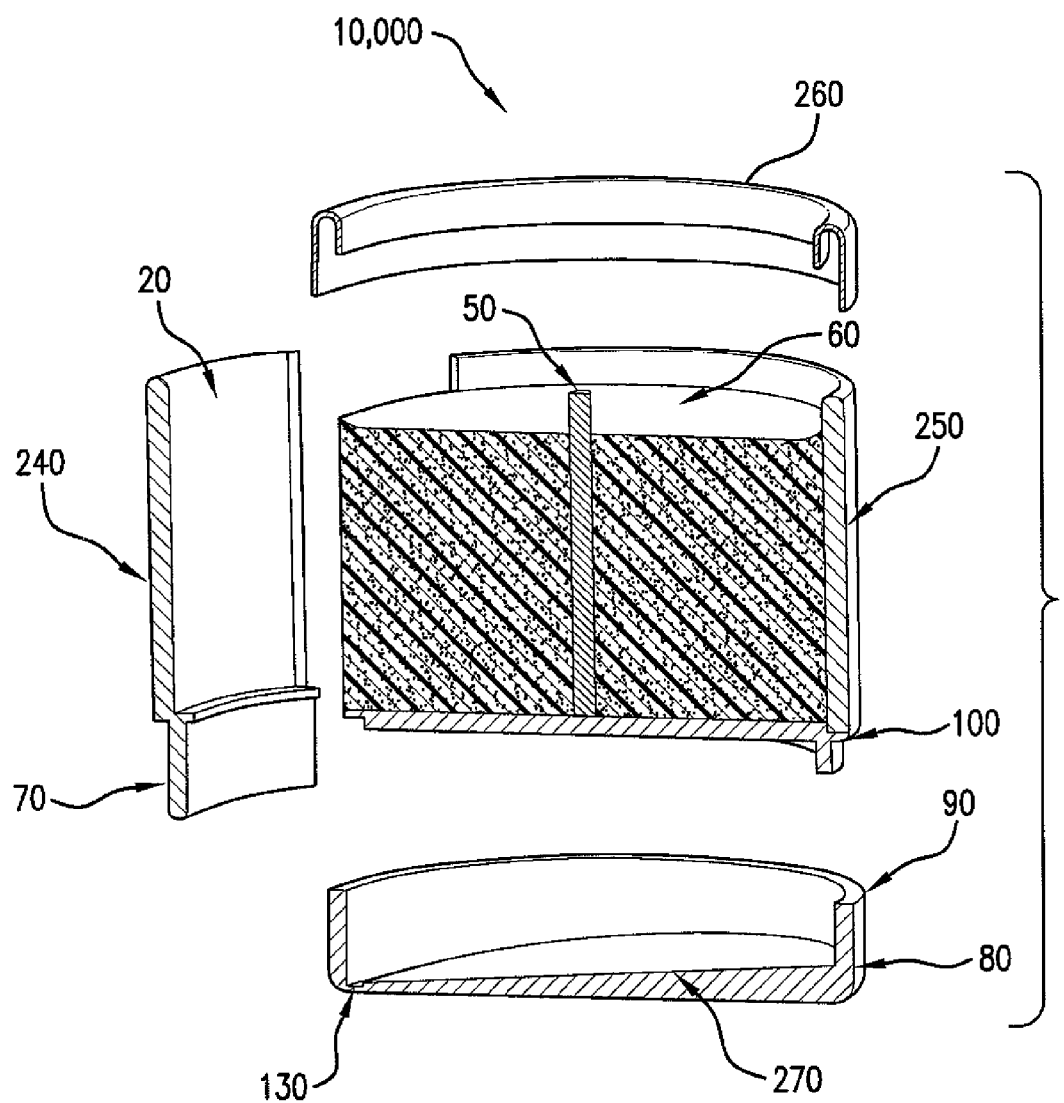
FIGS. 10-12 depict a still further embodiment of the presently disclosed subject matter, in which the hollow vessel includes both porous sidewall components, and non-porous sidewall components, bound by a binding collar.

The exploded crosscut view of FIG. 10 depicts a vessel created with both a porous sidewall component (240) and a non-porous sidewall component (250) which when joined together form a complete vessel capable of containing an independent fragrance medium, such as a candle or gel as described in the previous embodiments.

An advantage of the embodiment shown in FIG. 10 is that in all prior embodiments, the hollow vessel, or at least the substrate of the hollow vessel, was exclusively porous. The current embodiment offers the option of creating a vessel in which at least a portion of which is fabricated from materials which are not porous such as, but not limited to, metal, glass, a thermoplastic, and the like.

The ability to insert a segment of the vessel fabricated from a porous composition such as ceramic, terracotta, clay earthenware, concrete, porcelain into a partially formed vessel fabricated from non-porous materials offers flexibility in the creation of unique diffusing devices.

Previous embodiments disclose the use of materials which are and opaque. In the current embodiment the option now exists to create a container fabricated from transparent or translucent glass in combination with a portion fabricated from a porous material. This offers many advantages especially when the vessel is used as container for a fragranced candle.

As depicted in FIG. 10 there is a portion of a container (10,000) manufactured from a non-porous sidewall composition (250) such as glass or a metal. A portion of the container is also depicted as being made with a porous sidewall (240) such as terracotta.

The porous sidewall components and the nonporous sidewall components could be slideably engaged or they could be mechanically joined by inserting them in the reservoir base (80) and using a binding collar (260) which slips over the top of the vessel to keep the sections in locking contact.

It is important that the union between the two components have sufficient integrity so as to contain the contents of the air freshening composition fluidly filled into the vessel (here, a candle (60) with a wick (50)) and until such time as this composition develops the consistency of its final form.

The interior surface of the porous sidewall component (240) of the vessel is provided with a glazed coating (20) on its interior surface to prevent the air freshening medium poured into the vessel (e.g., a candle) from penetrating the absorbent porous composition of this component.

The porous sidewall component (240) of the vessel also differs from the non-porous sidewall component (250) in that there are wicking extensions (70) which extend downward from the porous sidewall component (240) into the detachable reservoir base (80) of the unit. As opposed to a convex surface, a slanted surface (270) is provided along the bottom of the base to direct the liquid fragrance composition housed in reservoir base to the wicking extension that extends from the porous side wall component. The reservoir base (80) is also provided with a reservoir base upper lip (90) and a recessed channel (130). A recess (100) is also provided in the hollow vessel so as to properly position the sidewall component within the reservoir base.

FIG. 10 depicts the engagement of the composite hollow vessel (10) with the wicking extensions (70) fully residing in the recessed channel (130) formed to accept them. The liquid reservoir composition (140) has been loaded into the reservoir base (80) in a separate loading process.

The liquid reservoir composition (140) now in contact with the wicking extensions (70) can freely migrate up into the porous surfaces of the porous sidewall component (240) of the vessel for eventual evaporation. Complete contact between the fluid reservoir composition (140) and the wicking extension (70) in the reservoir base (80) is facilitated by the slanted surface (270) on the interior of the reservoir base (80) which directs the fluid contents of the reservoir base (80) towards the recessed channel (130) for continuous contact with the wicking extension (70).

In the event that the liquid reservoir composition (140) is in excess such that the porous component (240) of the vessel becomes saturated before all of the reservoir fluid migrates out of the reservoir base (80), the porous sidewall component (240) of the vessel will be continually replenished with the reservoir composition as the surface of the porous sidewall component (240) becomes depleted and accepting of replenishment in a continuous wicking process. This process will continue until such time as the liquid fragrance composition (140) constituting the fluid reservoir is fully evacuated from the reservoir base (80).

Figure 11:
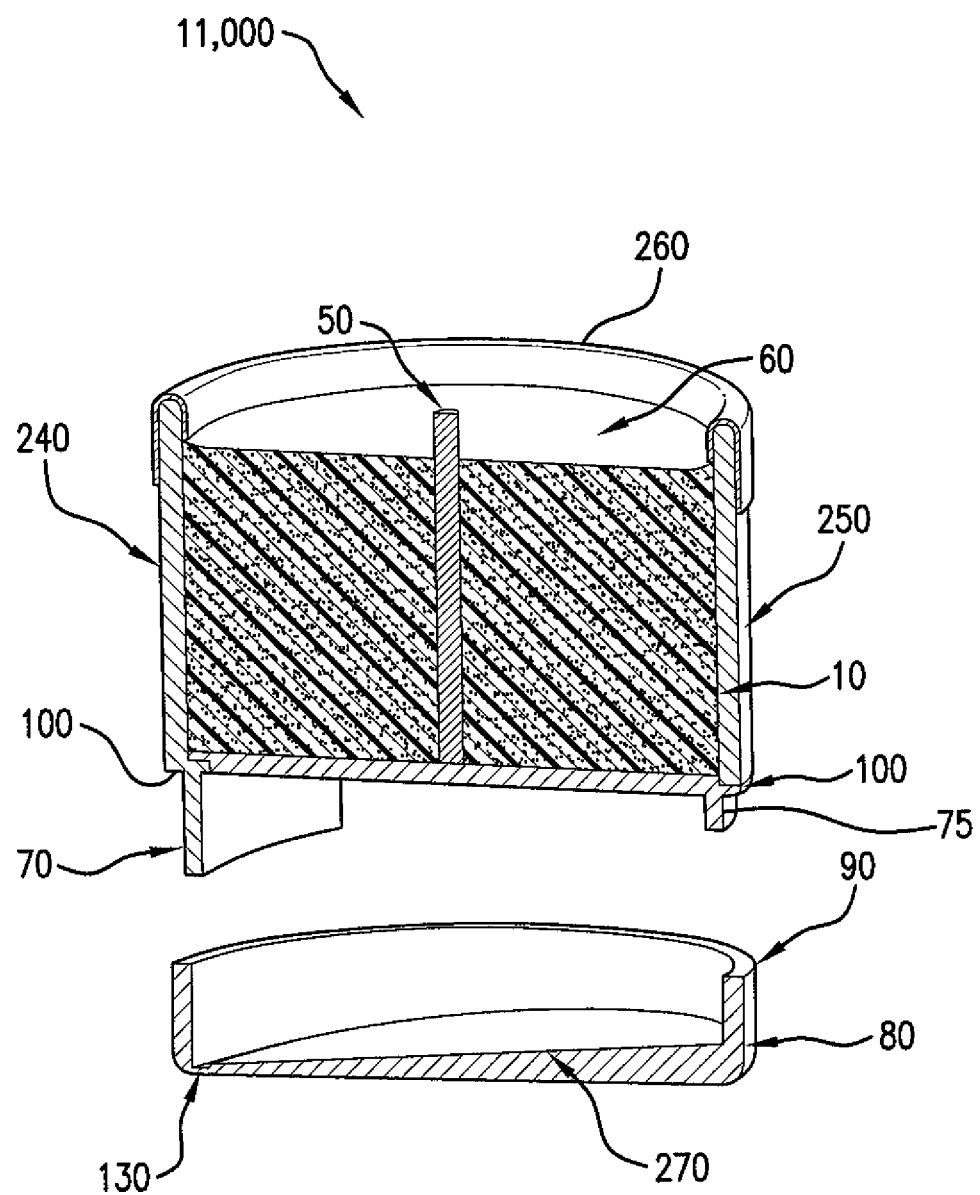

Another unit (11,000) according to one embodiment of the present application is shown in FIG. 11. A hollow vessel (10) is provided containing a candle (60) and candle wick (50). As in FIG. 10, a porous sidewall components (240) and nonporous sidewall component (250) is provided. A wicking extension (70) extends from the porous sidewall component. Recesses (100) are provided for both sidewall components for proper positioning of the wicking extension (70) and an extension (75) from the nonporous sidewall component with the reservoir base (80). A binding collar (260) is provided to maintain structural integrity between the porous sidewall component and the nonporous sidewall component. The reservoir base (80) is provided with a reservoir base upper lip (90), a recessed channel (130) and a slanted surface (270).

Figure 12:
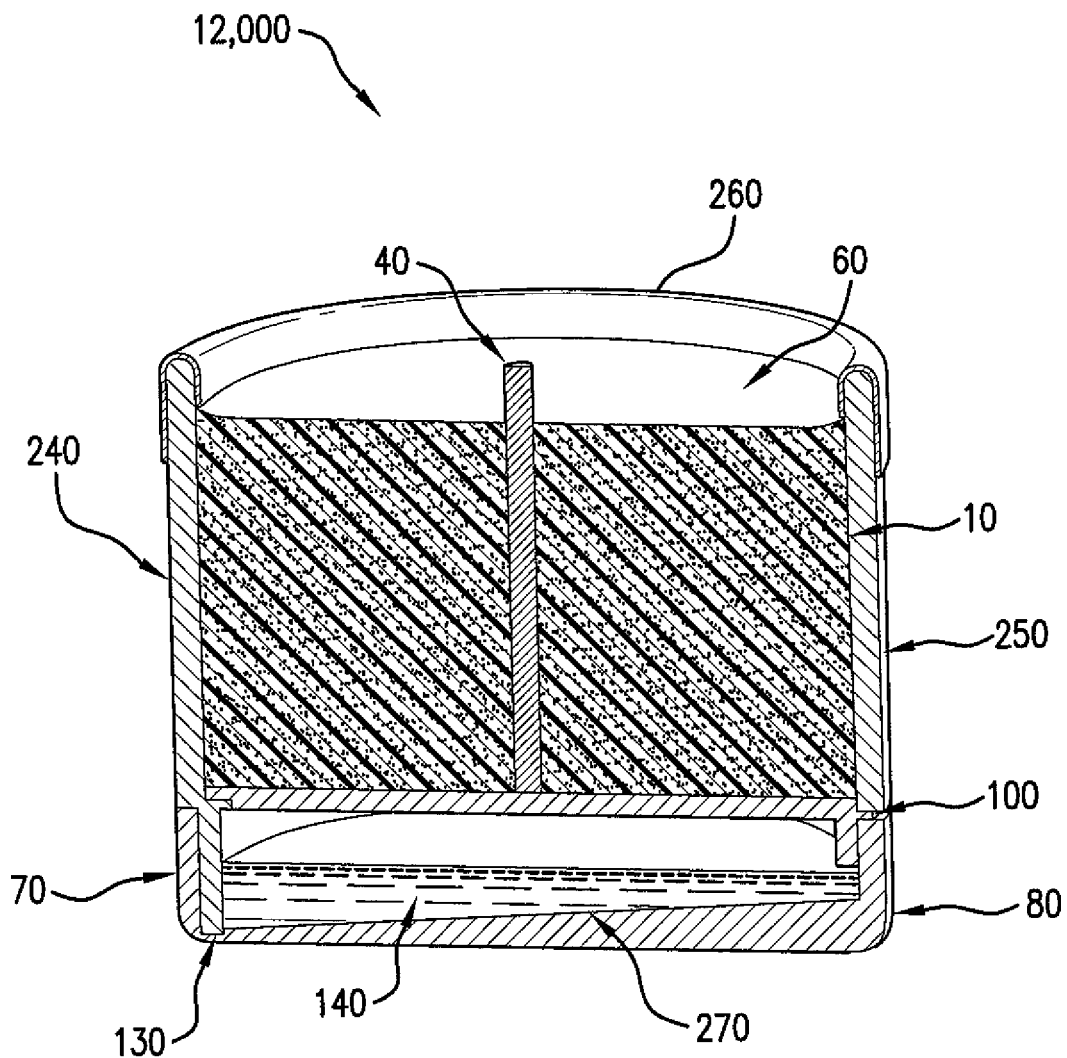

FIG. 12 depicts an embodiment (12,000) of the present application in which the hollow vessel (10) includes both a porous sidewall component (240) and a nonporous sidewall component (250). A binding collar (260) joins the porous sidewall component and nonporous sidewall component. The hollow vessel contains a candle (60) and candle wick (40). A wicking extension (70) extends from the porous sidewall component, set in from the reservoir base (80) via a recess (100). Because this embodiment includes only one wicking extension, a slanted surface (270) is provided to direct the reservoir liquid composition (140) to the wicking extension.

Figure 13:
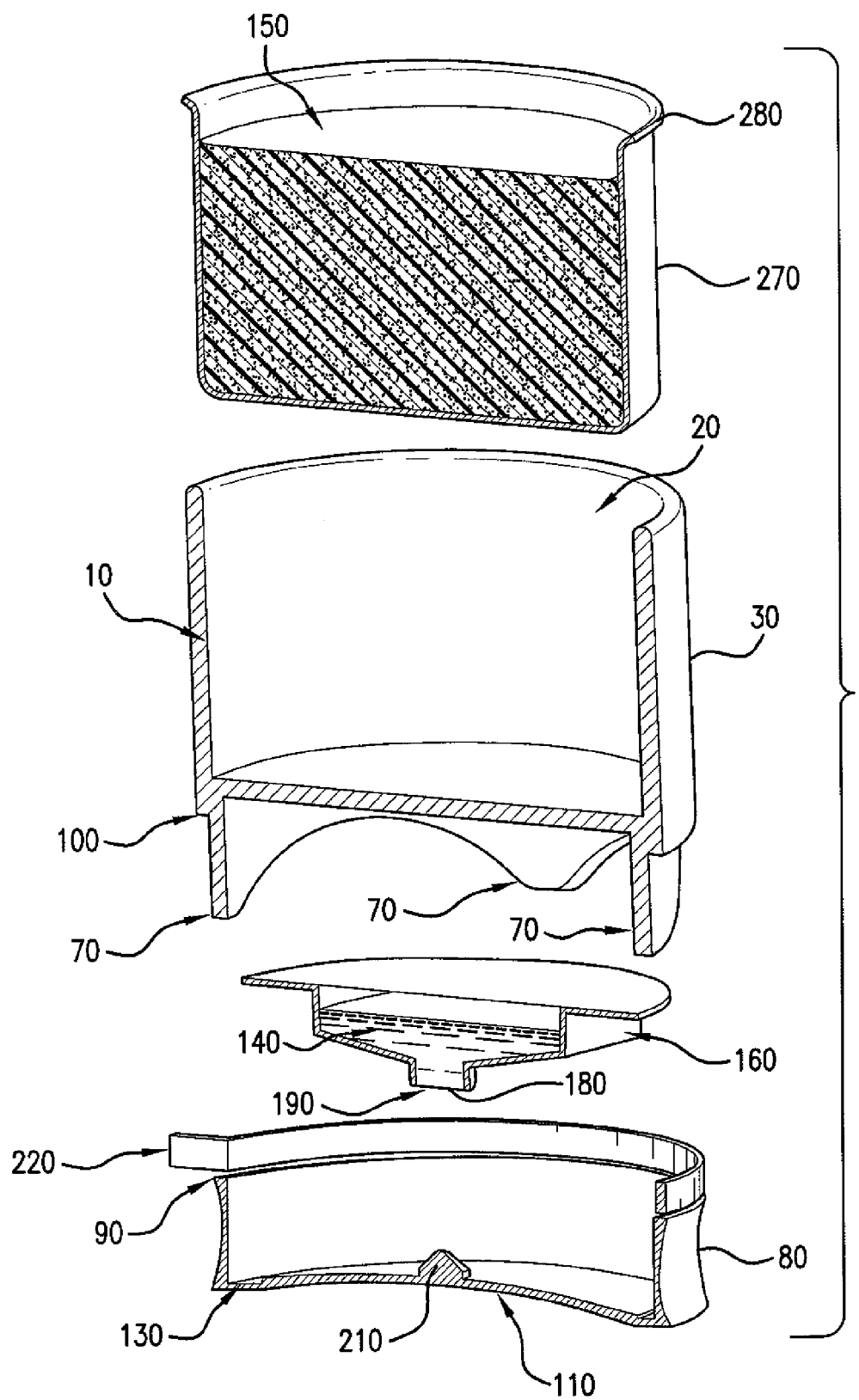
FIGS. 13 and 14 provide an alternative embodiment of the present application, in which a secondary container is provided to house the first fragrance medium (here a gel composition), for ultimate disposition in the hollow vessel.

FIG. 13 depicts an exploded crosscut view of a unit in which a gel composition (150) is filled into the confines of a secondary container (270), each of which being contained in the hollow vessel (10). The secondary container (270) is fabricated from a non-porous composition such as a thermoplastic, or other materials that would also prove suitable. Once the secondary container (270) is filled with a suitable air freshening medium of choice it can then be inserted into the hollow vessel (10).

A flange (280) surrounds the open circumference of the secondary container (270) such that when the secondary container (270) is loaded into the hollow vessel (10), the flange (280) will be supported by the uppermost open edge at the top of the hollow vessel (10).

Although shown in exploded view, a reservoir insert or cartridge (160) is provided and ultimately affixed to the bottom of the hollow vessel. The reservoir cartridge is provided with a narrow opening (190) with a ruptureable foil seal (180), positioned for engagement with a piercing lance (210), which is provided along the bottom of the reservoir base (80). Upon removing the tear away band (220), the recess (100) will rest on the reservoir base upper lip (90), and the foil seal will be torn, thereby emptying the reservoir liquid composition (140) into the reservoir. A convex surface (110) is provided along the bottom of the reservoir to direct the reservoir liquid composition to the recessed channel (130). The bottom of the wicking extensions (70) will ultimately be disposed in the recessed channel.

The secondary container (270) can be used to contain a gel composition or a candle but could also be used to contain other independent fragrance mediums, such as, but not limited to, potpourri, liquid wicks, fragrance membranes and fragranced polymer beads.

Figure 14:
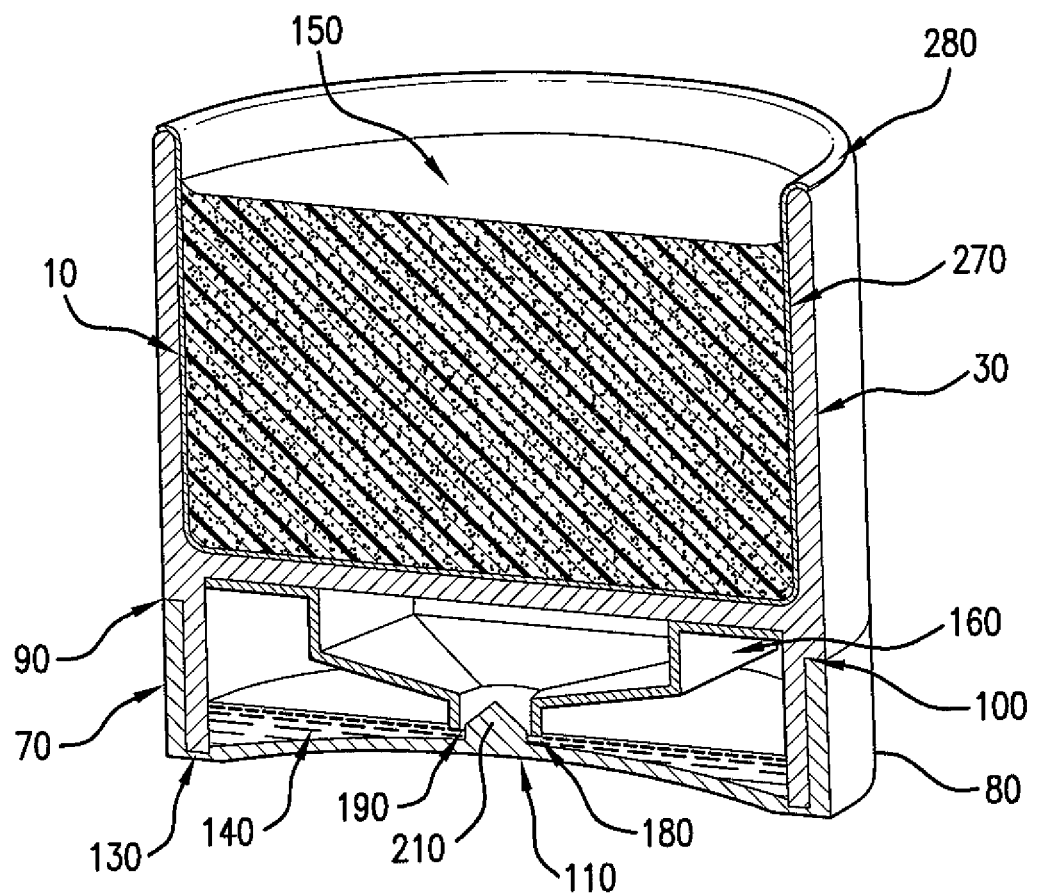

FIG. 14 depicts a crosscut view of the unit fully engaged and activated. An insertable reservoir (160) is loaded with a fragrance composition (140) and lockably attached to the base of the hollow vessel (10).

The tear-away band (FIG. 13, 220) has been removed to allow the base to travel upward and in the process have the piercing lance (210) rupture the foil seal (180) over the narrow opening (190) of the fragrance insert (160). The reservoir fluid (140) will drain into the base (80) and consequently contact the wicking extensions (70). The hollow vessel is provided with a recess (100), which joins the reservoir base upper lip (90) such that the porous vessel sidewall and reservoir sidewall form a substantially continuous plane.

A flange (280) is also provided along the outer opening of the hollow vessel. A secondary container (270) is also provided to contain the gel composition (150), both of which are contained in the hollow vessel.

Figure 15:
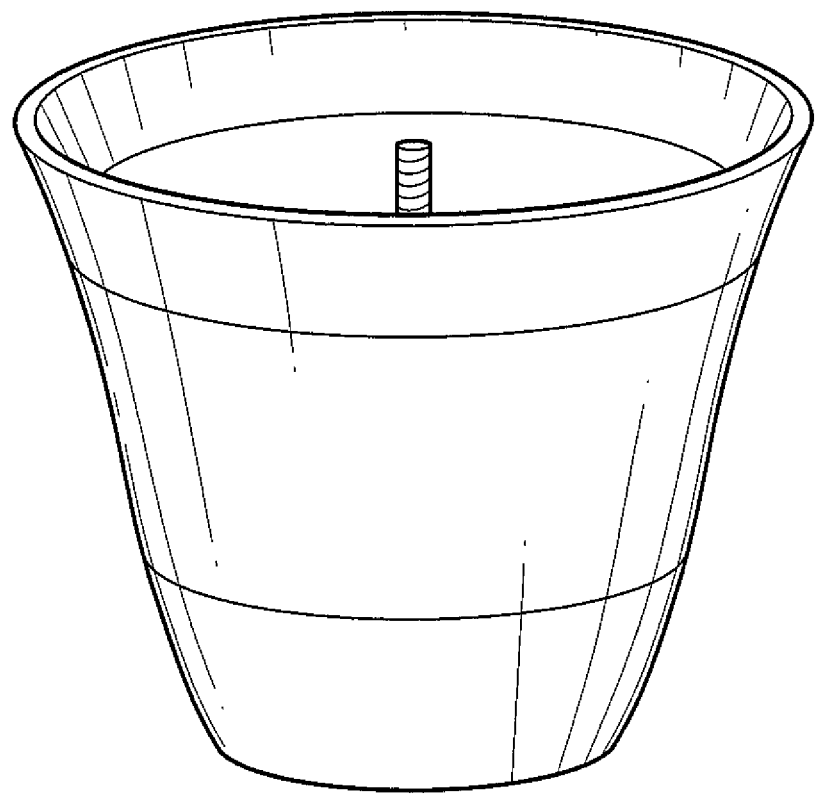
FIG. 15 depicts an assembled fragrance delivery device according to one embodiment of the present application.

FIG. 15 provides a depiction of a device according to one embodiment of the present application. An exploded view of the device (16,000) is provided in FIG. 16. A glazed coating (10) is provided along the interior of the hollow vessel. A glaze coating (20) is also provided along a portion of the exterior of the hollow vessel. Glaze is further provided along the reservoir rim (40) and the inner reservoir surface (30).

Figure 17:
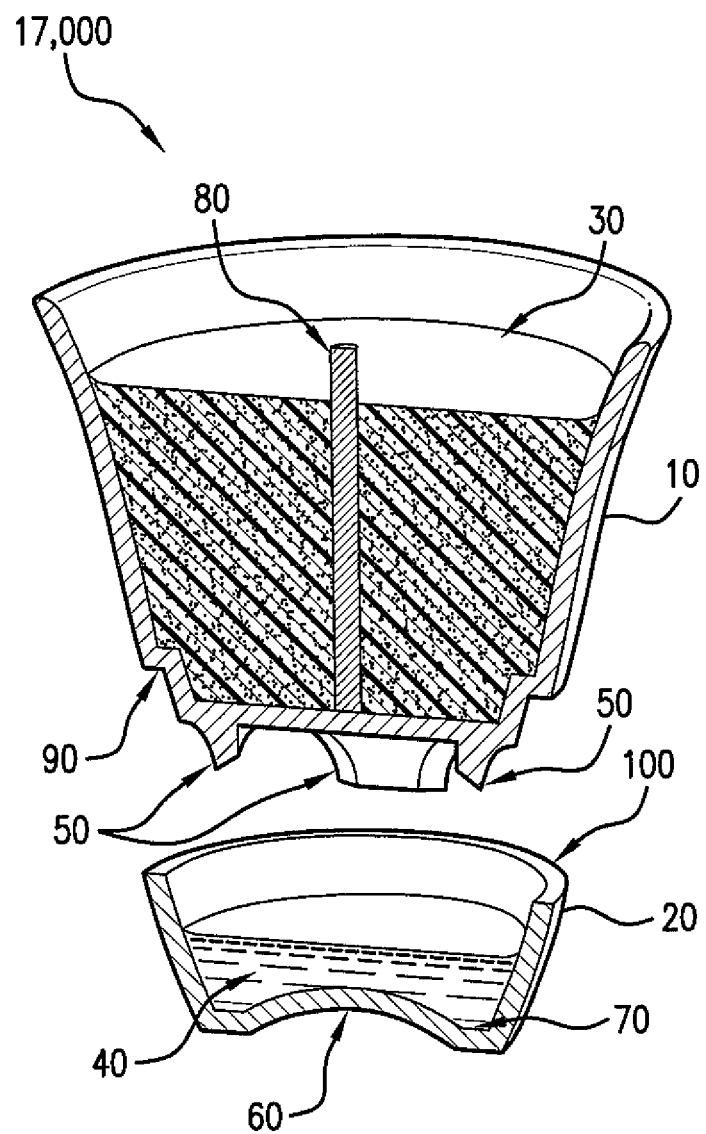
FIG. 17 depicts an exploded view of a fragrance delivery device according to one embodiment of the present application.

FIG. 17 provides a device (17,000) according to an alternative embodiment of the present application in which three wicking extensions or protrusions (50) are provided. In this embodiment, a wax candle (30), provided with a candle wick (80), is included as the first fragrance medium. The candle is contained in a hollow vessel (10). A recessed groove (90) is provided which ultimately engages with the reservoir rim (100). The reservoir (20) contains a liquid fragrance composition (40). The bottom of the reservoir as a convexed surface (60) so as to direct the liquid fragrance composition to a channel (70), which is formed along the outer periphery of the bottom of the reservoir.

Figure 18:
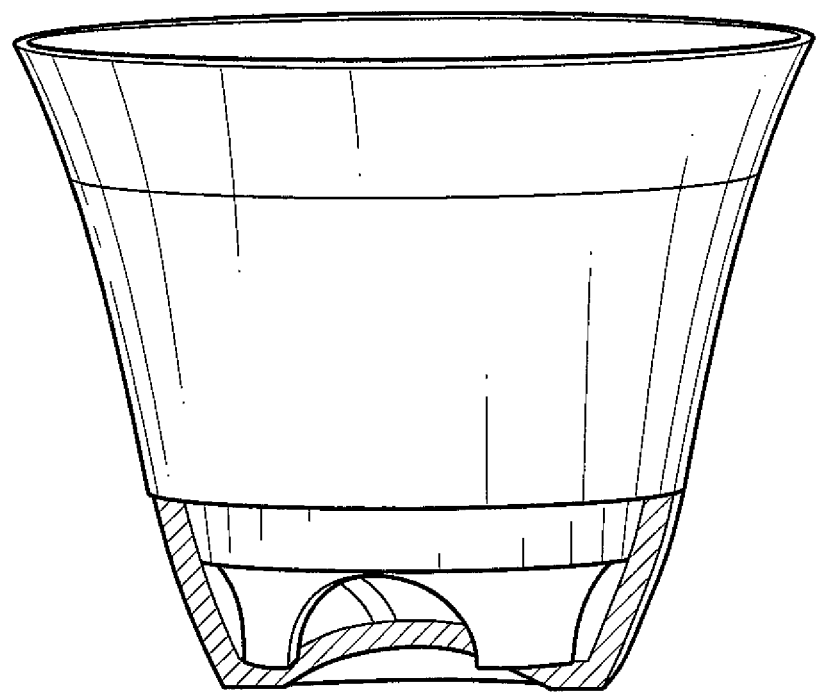
FIGS. 18 and 20 depict a crosscut view of a fragrance delivery device according to one embodiment of the present application in which three wicking extensions are provided for engagement with the reservoir.
Figure 19:
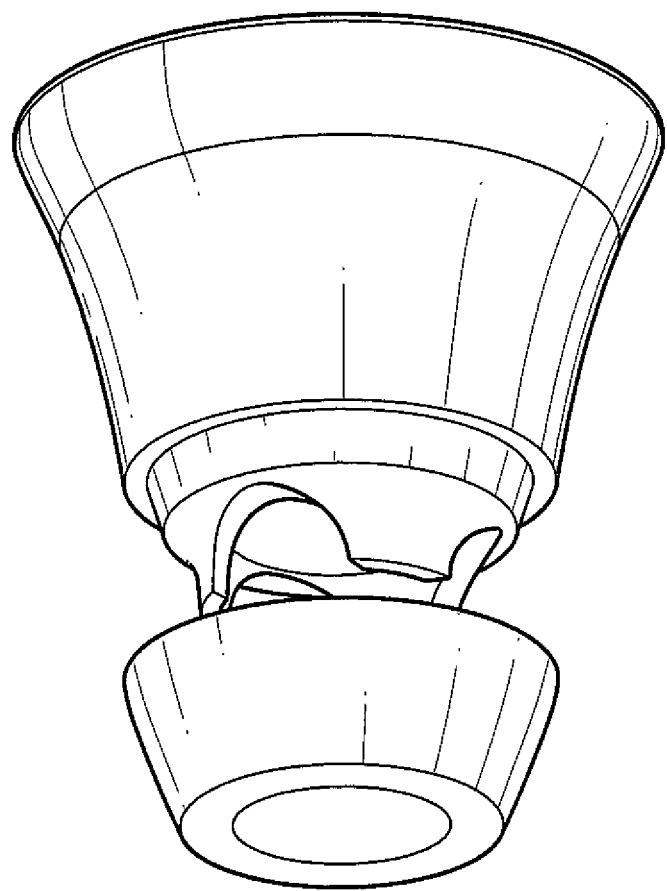
FIG. 19 provides a view of the outside of a fragrance delivery device according to one embodiment, in which an optional glaze is provided.

FIGS. 18 and 19 provide an assembled view of an embodiment in which three wicking extensions or protrusions are provided.

Figure 20:
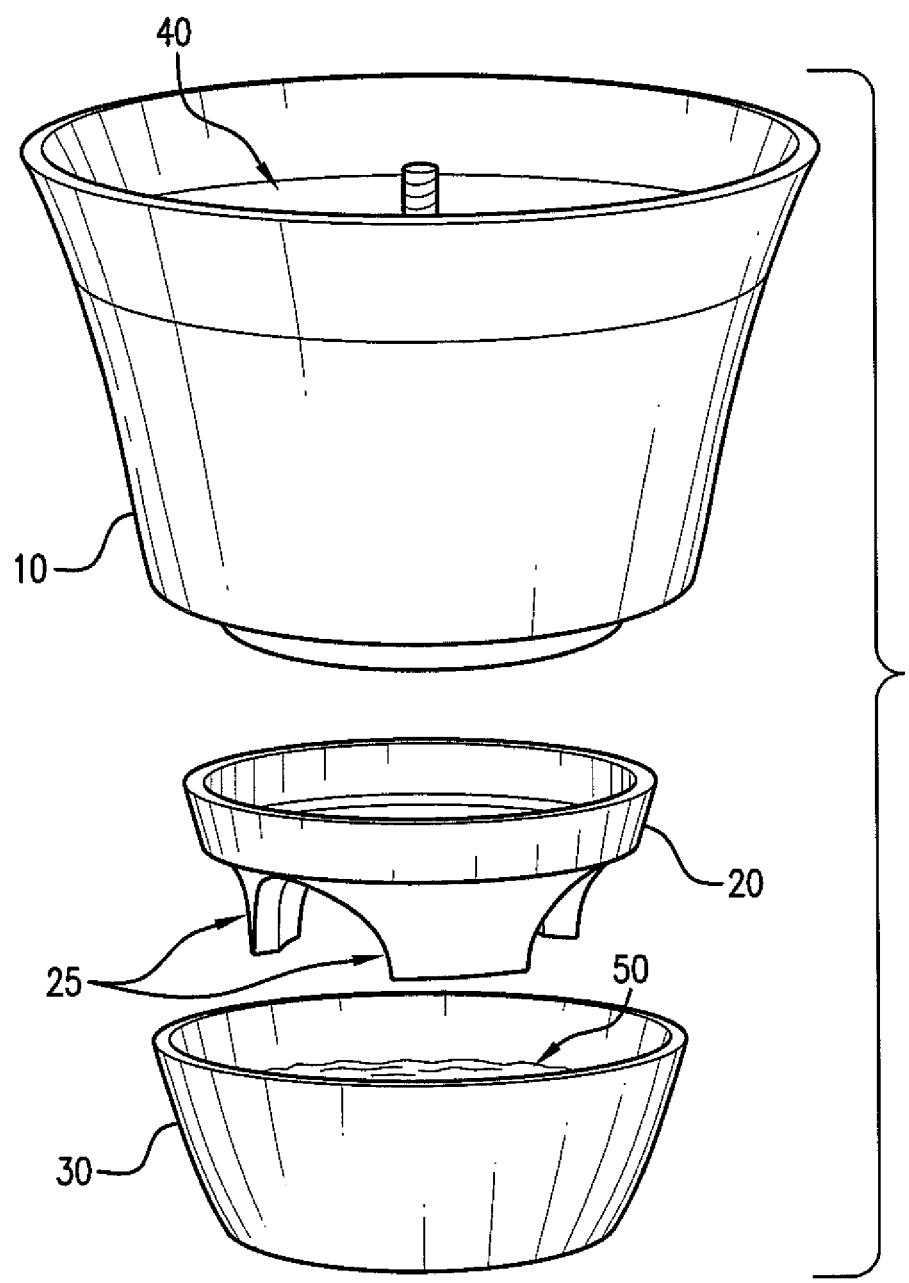

FIG. 20 provides another view of a device (20,000) according to one embodiment of the present application, in which the wicking protrusions or wicking extensions (25) are provided as a separate member (20). The hollow vessel (10) contains a wax candle (40) and is designed to fit with both the separate member (20) containing the wicking extensions, and the liquid reservoir (30), which contains a liquid fragrance composition (50). As combined, sidewalls of the hollow vessel (10), separate member (20) and reservoir (30) form a substantially continuous plane.

FIG. 21 provides two alternative embodiments (21,000, 21,500) of the device of the present application. The hollow vessel (10) may be constructed of a liquid impervious material with absorbent sheathing (20). In this case the absorbent sheathing or members (30) could partially (as in 21,500) or entirely (as in 21,000) encompass the outside surface of the vessel and serve as means to absorb the liquid fragrance composition contained within the reservoir. With such a design, the hollow vessel 10 is constructed from an impervious material sheathed in an absorbent material to absorb the volatile liquid mixture 50 from the wicking protrusions 20 which are immersed in the liquid mixture contained in the liquid reservoir base. This exposure will allow the volatile liquid to evaporate and emanate from the exposed surface of the porous sheathing.

The three piece design of the device depicted in FIGS. 20 and 21 can also posses the advantage of being more cost effective, as it could simplify the manufacturing process, thus lowering the cost to produce.

A further variant to the examples detailed in FIGS. 20 and 21, the device can also be configured whereby the candle vessel and the wicking protrusions are both entirely constructed of a liquid impervious material. Such a device would be equipped with an absorbent sheathing or members that partially or wholly encompass the outside of the hollow vessel and wicking protrusions. With such a design, the hollow vessel is sheathed in an absorbent material to absorb the volatile liquid mixture from the wicking protrusions, which are also sheathed in an absorbent material to absorb the liquid mixture contained in the liquid reservoir base. This exposure will allow the volatile liquid to evaporate and emanate from the exposed surface of the porous sheathing. The porous material may include, for example, porous plastics and fibrous materials, such as cellulose and polyesters.

The operation of the present application is multifunctional by design in that it combines, for example, a candle or fragranced gel delivery device with a porous vessel to wick and simultaneously emanate a volatile liquid fragrance composition. Hence, continuous delivery of a fragrance or volatile liquid mixture is achieved, regardless of candle operation. Functions of a candle design include illumination and fragrance delivery form the wax. A secondary function of the burning candle warmth would be to assist in the volatilization of the liquid components residing in the porous walls of the candle vessel. This improved delivery of volatile materials would be most evident with the higher molecular weight or higher boiling components of the reservoir base fragrance. In addition, the multifunctional design encompassing a candle with a liquid wicking feature in a single device would permit creative delivery of volatiles possessing unique characteristics unto themselves and in combination. Applications of this device include, but are not limited to, air-care, malodor elimination, aromatherapy, medicates, and any other composition containing volatile components.

The benefit of having fragrance emanation from both the porous sidewalls of the vessel as well as form the gel composition contained within it results in a highly impactful fragrance dispensing device. Accordingly, embodiments of the present application also provide a method of delivering a fragrance that includes loading the device with a liquid fragrance composition and allowing the fragrance to emanate to the ambient space surrounding the device.

The fragrance compositions that may be used include commercially available fragrances. Fragrances available from Takasago International Corporation are particularly preferred.

Also, malodor control compositions may be used in the liquid-evaporate delivery device of the present application, either alone or in combination with a fragrance composition. Accordingly, the liquid-evaporate delivery device may be used to neutralize and/or control odors, instead of, or in addition to, providing a hedonically pleasing odor to the surrounding air space. Use of malodor control compositions may find utility in bathroom and kitchen applications, and other areas in which malodors are likely to be present.

The liquid-evaporate delivery device may also deliver insecticides or insect repellents. Insect repellents and insecticides known to those of ordinary skill in the art can be used. Preferred insect repellent compositions include insect repellent compositions containing para-menthane diol, commercially available from Takasago International Corporation U.S.A. (Rockleigh, N.J.).

Gels could also be used in the liquid-evaporate delivery device of the present application. The gels could be, for example, fragrance gels or therapeutic gel (e.g. aloe vera gel, essential oil gels).

The device of the present application may be applied to household rooms and used as an air freshener. Alternatively, the liquid-evaporate delivery device may be used in an office environment (e.g. at reception areas), or a place of business (e.g. a reception area) or a place of recreation (e.g. a casino).

Examples

The present application is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

A panel of sensory experts evaluated the intensity of fragrance of burned and unburned candles that were placed in a 800 cubic foot room for 30 minutes prior to evaluation. The panel evaluated the strength of fragrance on a 1-9 scale, 1 being the weakest. The candles were evaluated initially, and 1 week and 2 weeks later. The following candles were analyzed:

[Medium A—Candle alone]—fruity fragranced, commerically available candle alone;

[Medium B—Candle+Fragranced Ceramic Vessel]—fruity fragranced, commerically available candle contained within a ceramic container that is communication with 8 grams of fragrance solution via wicking extensions

[Medium B'—Candle+Fragranced Cermaic Vessel]—identical to Medium B, yet immersed porous vessel sidewall immersed in fragrance to simulate saturated condition]

[Medium C—Candle+Unfragranced Glass Vessel]—fruity fragranced, commerically available candle contained within a glass container The following results were reported by the panel:

| | Unburned Candles | | | | | |
|---|---|---|---|---|---|---|
| | Initial Evaluation | | 1 Week Evaluation | | 2 Week Evaluation | |
| Fragrance Medium | Fragrance Rating | Comment | Fragrance Rating | Comment | Fragrance Rating | Comment |
| A (Candle Alone) | 1 | Very little or no fragrance detected | 1 | | 1 | |
| B (Candle + Fragranced Vessel) | 7 | Significant fragrance detected | 6 | | 6 | |
| B' (Candle + Fragranced Vessel) | 7 | Equal to strength of Medium B | 4 | Slightly weeker than previous week | 3 | |
| C (Candle + Unfragranced Vessel) | 1.5 | Noticeable but weak fragrance detected | 1 | No fragrance detected | 1 | No fragrance detected |

| | Burned Candles | | | | | |
|---|---|---|---|---|---|---|
| | Initial Evaluation | | 1 Week Evaluation | | 2 Week Evaluation | |
| Fragrance Medium | Fragrance Rating | Comment | Fragrance Rating | Comment | Fragrance Rating | Comment |
| A (Candle Alone) | 6.5 | Significant fragrance detected | 6 | Slightly weaker than previous week but sill significant fragrance detected | 7 | Significant fragrance detected |
| B (Candle + Fragranced Vessel) | 7 | Significant fragrance detected | 7 | Significant fragrance detected; comparable to initial evaluation | 6 | Slightly weaker than previous week but still significant fragrance detected |
| C (Candle + Unfragranced Vessel) | 6.5 | Significant fragrance detected, comparable to Fragrance Medium B | 5 | Weaker than previous week but still significant fragrance detected | 6 | Candle performance comparable to Fragrance Medium B |

The fragranced vessel, i.e. the vessel that is in communication with fragrance from the reservoir via wicking extensions, adds fragrance intensity, as compared to the unfragranced vessel. The fragranced vessel significantly adds to the fragrance intensity when the candle is in the unburned state.

The above-mentioned patents, applications, test methods, and publications are hereby incorporated by reference in their entirety.

Many variations of the present application will suggest themselves to those skilled in the art in light of the above detailed description. All such obvious variations are within the fully intended scope of the appended claims.

What is claimed:

1. A fragrance delivery device comprising:
    (a) a hollow vessel containing a first fragrance medium and further comprising a porous exterior surface with a porous wicking extension extending therefrom; and
    (b) a reservoir containing a second fragrance medium, the second fragrance medium in fluid communication with the wicking extension and the porous exterior surface.

2. The fragrance delivery device of claim 1, wherein the first fragrance medium is selected from a candle, a gel composition, fragranced membranes, polymer beads, a liquid fragrance medium with an exposed wick, and fragranced potpourri.

3. The fragrance delivery device of claim 1, wherein the first fragrance medium is a candle.

4. The fragrance delivery device of claim 1, wherein the porous exterior surface is selected from a ceramic, terracotta, clay earthenware, concrete and porcelain.

5. The fragrance delivery device of claim 1, wherein at least a portion of the exterior porous surface is coated with a non-porous glazed layer.

6. The fragrance delivery device of claim 1, wherein the hollow vessel further comprises a non-porous surface.

7. The fragrance delivery device of claim 5, wherein the non-porous surface is selected from a mirror, a glass, a metal, and a thermoplastic.

8. The fragrance delivery device of claim 1, wherein the second fragrance medium is a liquid fragrance composition.

9. The fragrance delivery device of claim 1, wherein the hollow vessel is adapted to be disposed over the reservoir and wherein the hollow vessel and the reservoir are at least substantially co-centric.

10. The fragrance delivery device of claim 9, wherein the porous wicking extension is disposed within a channel formed along the outer periphery of the bottom of the reservoir.

11. The fragrance delivery device of claim 10, wherein the bottom of the reservoir has a convexed surface so as to direct the second fragrance medium to the channel formed along the outer periphery of the bottom of the reservoir.

12. The fragrance delivery device of claim 1, wherein the reservoir further comprises a piercing lance.

13. The fragrance delivery device of claim 12, wherein the reservoir further comprises a tear away band.

14. The fragrance device of claim 12, wherein the hollow vessel has a fragrance cartridge affixed the bottom thereof, the fragrance cartridge comprising a rupturable seal positioned for engagement with the piercing lance.

15. The fragrance delivery device of claim 1, wherein the porous exterior surface, and porous wicking extension is provided by an absorbent sheath affixed to a liquid impervious substrate.

16. A fragrance delivery device comprising:
    (a) a hollow vessel containing a first fragrance medium and further comprising a porous exterior surface; and
    (b) a member comprising a porous wicking extension, the member adapted to engage with the hollow vessel; and
    (c) a reservoir containing a second fragrance medium and adapted to engage with the member comprising a porous wicking extension, the second fragrance medium in fluid communication with the wicking extension and the porous exterior surface.

17. The fragrance delivery device of claim 16, wherein the first fragrance medium is selected from a candle, a gel composition, fragranced membranes, polymer beads, a liquid fragrance medium with an exposed wick, and fragranced potpourri.

18. The fragrance delivery device of claim 17, wherein the first fragrance medium is a candle.

19. The fragrance delivery device of claim 17, wherein the second fragrance medium is a liquid fragrance composition.

20. The fragrance delivery device of claim 16, wherein the hollow vessel is adapted to be disposed over the reservoir and wherein the hollow vessel and the reservoir are at least substantially co-centric.

21. The fragrance delivery device of claim 16 wherein the reservoir further comprises a piercing lance and a tear away band.

22. The fragrance device of claim 21, wherein the hollow vessel has a fragrance cartridge affixed the bottom thereof, the fragrance cartridge comprising a rupturable seal positioned for engagement with the piercing lance.

* * * * *

UNITED STATES PATENT AND TRADEMARK OFFICE
CERTIFICATE OF CORRECTION

PATENT NO. : 8,695,891 B2  
APPLICATION NO. : 12/897316  
DATED : April 15, 2014  
INVENTOR(S) : Santini et al.

Page 1 of 6

It is certified that error appears in the above-identified patent and that said Letters Patent is hereby corrected as shown below:

In the DRAWINGS:

Delete Drawing Sheets 4, 5, 12 and 14, and replace with Drawing Sheers 4, 5, 12 and 14. (Attached)

In the SPECIFICATION:

Column 3, line 7

"FIG. 15 depicts an assembled fragrance delivery device"
should read --FIG 15 depicts a cross-cut view of a fragrance delivery device--

Column 3, line 9

Figure 16:
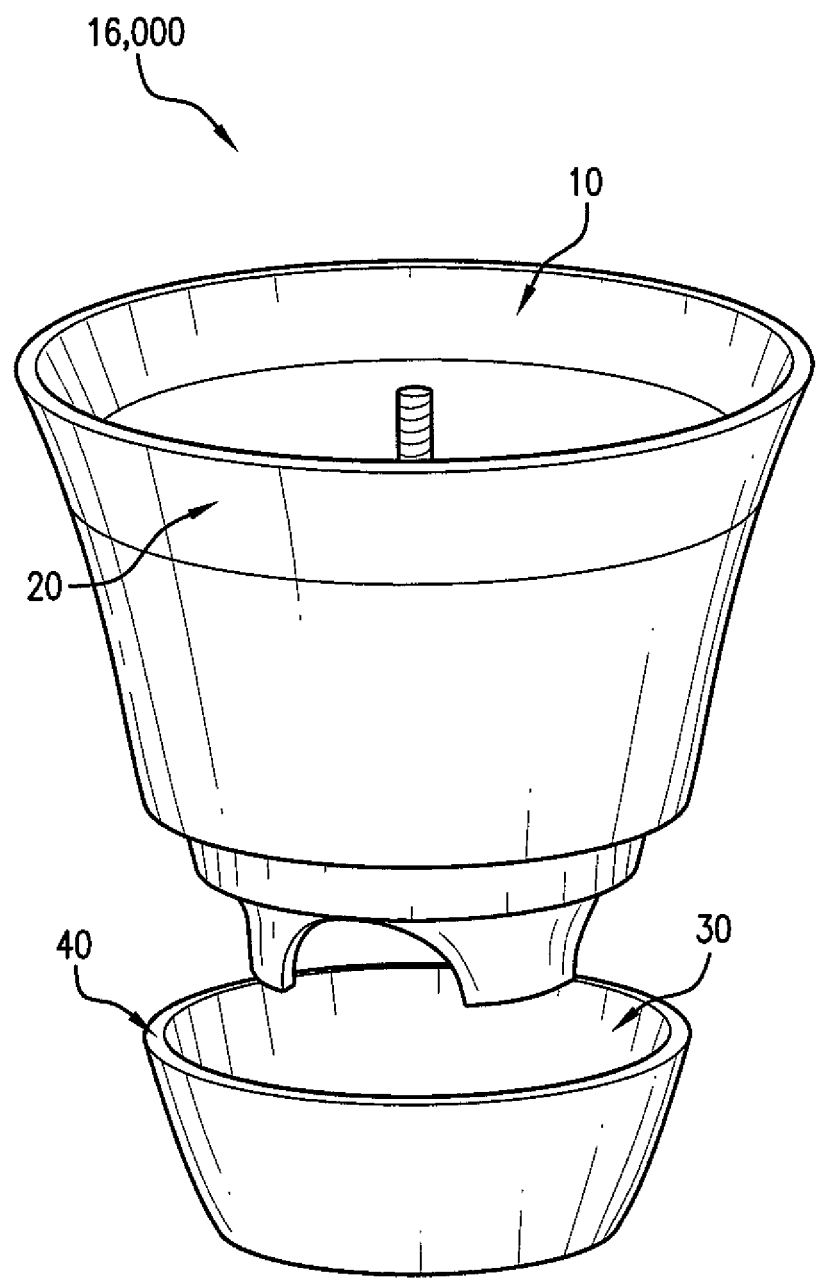
FIG. 16 depicts a cross-cut view of a fragrance delivery device according to one embodiment of the present application.

"FIG 16 depicts a cross-cut view of a fragrance delivery"
should read --FIG 16 depicts an assembled fragrance delivery--

Figure 21B:
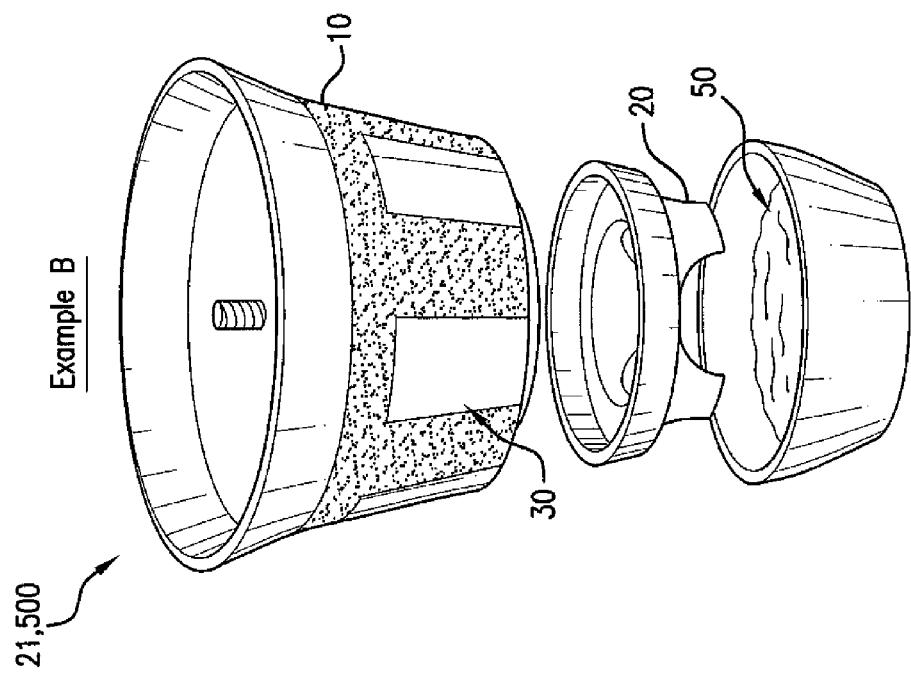
FIG. 21 provides still alternative embodiments of the present application in which a porous exterior surface is provided by absorbent sheaths bound to a liquid impervious substrate.
Figure 21A:
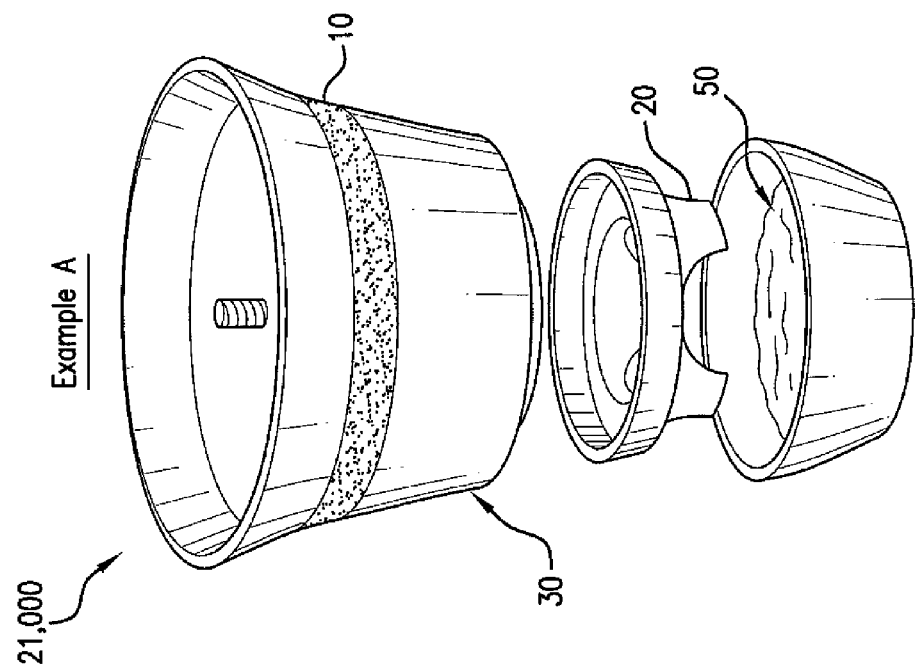
Figure 4:
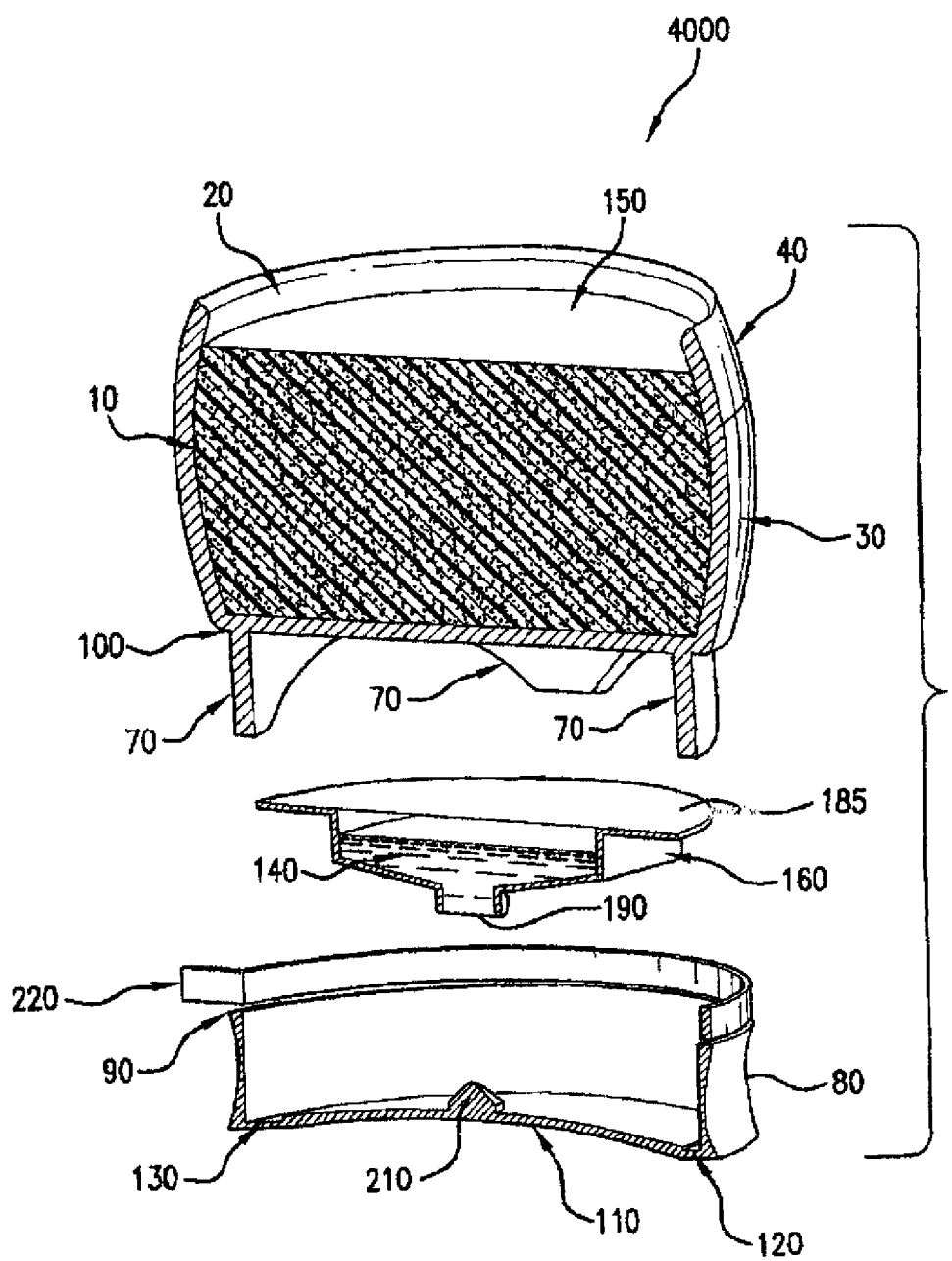
Figure 5A:
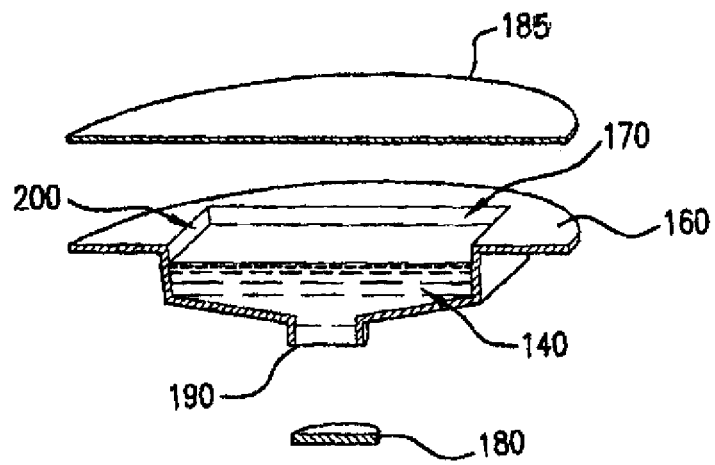
Figure 5B:
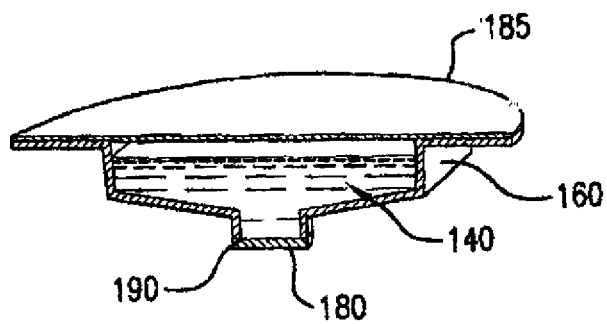
Figure 12:
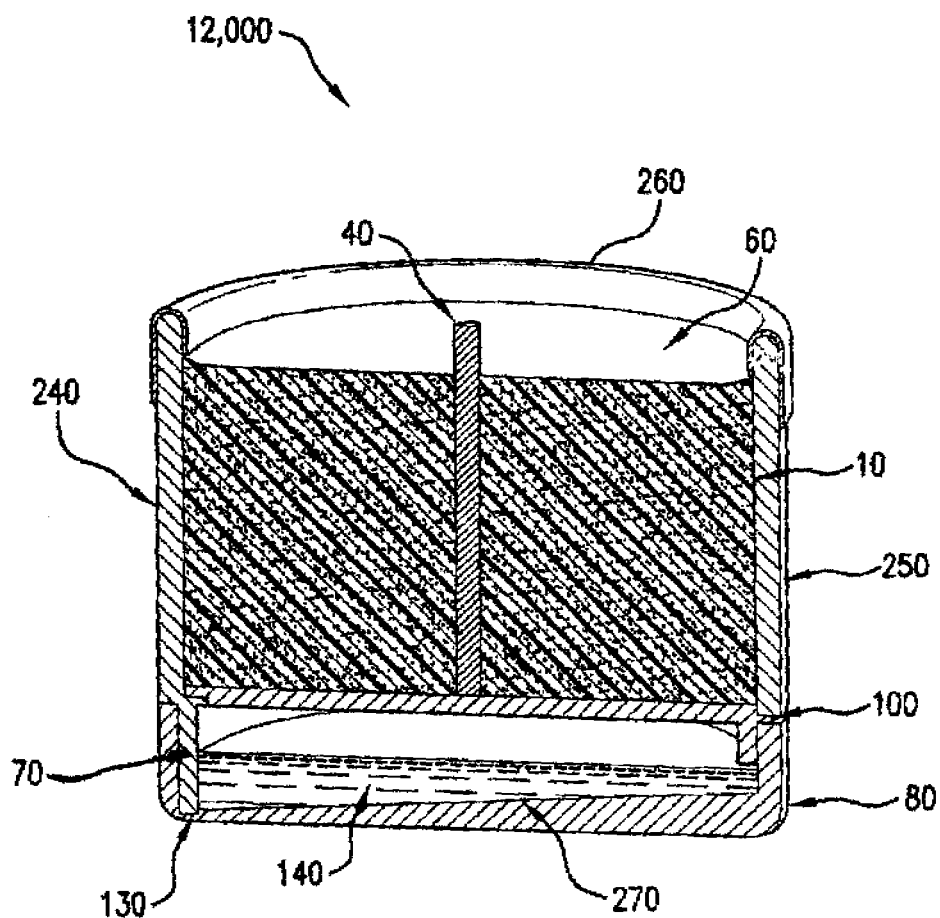
Figure 14:
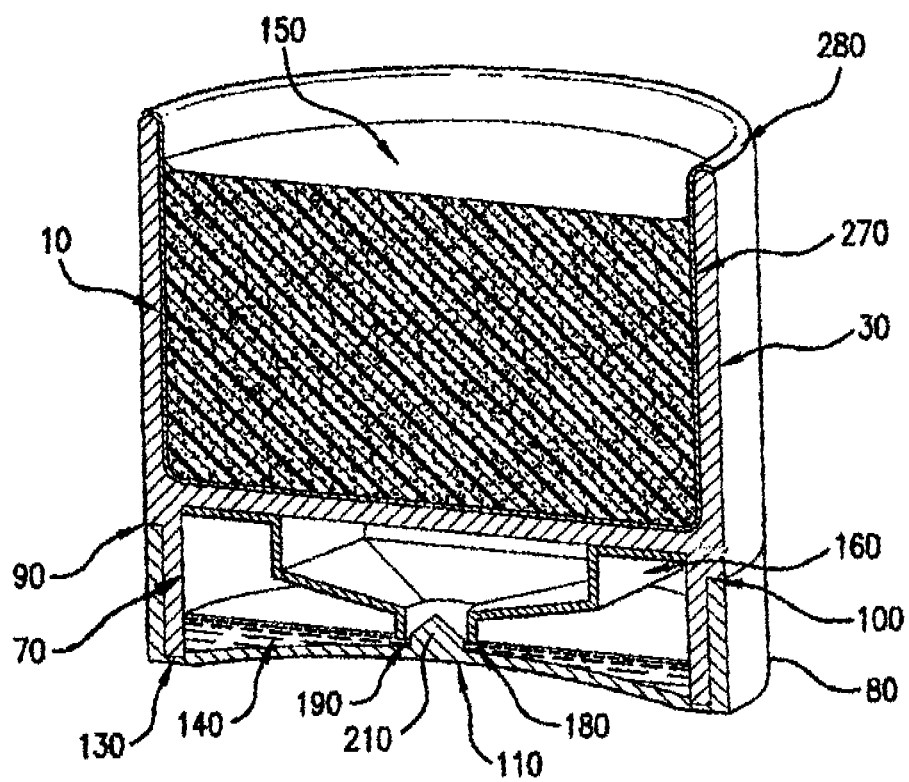

Column 3, line 23 delete "FIG. 21 provides still"    insert    --FIGS. 21A and 21B provide--

Column 3, Line 51       delete   "be" (second occurrence)

Column 4, Lines 10-11   delete   "or, in alternative embodiments, a solid fragrance composition (e.g., potpourri)

Column 6, Line 33       delete   "a rupturable"

Column 6, Line 34       delete   "(180)"   insert   --(185)--

Signed and Sealed this
Twenty-ninth Day of July, 2014

Michelle K. Lee
*Deputy Director of the United States Patent and Trademark Office*

CERTIFICATE OF CORRECTION (continued)
U.S. Pat. No. 8,695,891 B2

| | | | | |
|---|---|---|---|---|
| Column 6, Line 34 | delete | "(185)" | insert | --(180)-- |
| Column 6, Line 41 | delete | "(185)" | insert | --(180)-- |
| Column 6, Line 47 | delete | "(180)" | insert | --(185)-- |
| Column 6, Line 47 | delete | "(20)" | insert | --(200)-- |
| Column 8, Line 60 | delete | "and" | | |
| Column 9, Line 32 | delete | "FIG 10" | insert | --FIG 12-- |
| Column 11, Line 34 | delete | "FIG. 21 provides" | insert | --FIG. 21A and FIG 21B provide-- |
| Column 11, Line 37 | delete | "(20)" | insert | --(30)-- |
| Column 11, Line 51 | delete | "21" | insert | --21A and 21B-- |
| Column 11, Line 56 | delete | "21" | insert | --21A and 21B-- |
| Column 12, Line 12 | delete | "form" | insert | --from-- |
| Column 12, Line 28 | delete | "form" | insert | --from-- |
| Column 14, Line 11 | delete | "Cermaic" | insert | --Ceramic-- |

In the CLAIMS:

| | | | |
|---|---|---|---|
| Column 16, Claim 14, Line 10 | "affixed the bottom" | should read | --affixed to the bottom-- |
| Column 16, Claim 22, Line 46 | "affixed the bottom" | should read | --affixed to the bottom-- |